United States Patent
Weisbart

(12) 
(10) Patent No.: US 7,189,396 B1
(45) Date of Patent: Mar. 13, 2007

(54) DELIVERY SYSTEM USING MAB 3E10 AND MUTANTS AND/OR FUNCTIONAL FRAGMENTS THEREOF

(75) Inventor: Richard Weisbart, Los Angeles, CA (US)

(73) Assignees: The Regents of the University of California, Oakland, CA (US); The United States of America as represented by the Department of Veterans' Affairs, Washington, DC (US)

( * ) Notice: Subject to any disclaimer, the term of this patent is extended or adjusted under 35 U.S.C. 154(b) by 474 days.

(21) Appl. No.: 10/192,315

(22) Filed: Jul. 10, 2002

Related U.S. Application Data

(63) Continuation-in-part of application No. 09/142,142, filed as application No. PCT/US97/03785 on Mar. 7, 1997, now abandoned.

(60) Provisional application No. 60/013,297, filed on Mar. 8, 1996.

(51) Int. Cl.
 *A61K 39/395* (2006.01)
 *C07K 16/18* (2006.01)
 *C07K 16/44* (2006.01)

(52) U.S. Cl. .............................. 424/133.1; 424/134.1; 424/135.1; 424/141.1; 424/152.1; 530/391.7

(58) Field of Classification Search ............. 424/133.1, 424/134.1, 135.1, 141.1, 152.1; 530/391.7
See application file for complete search history.

(56) References Cited

U.S. PATENT DOCUMENTS 4,623,627 A    11/1986   Huang et al. ............... 435/240

OTHER PUBLICATIONS

Rudikoff, S. et al. Proc. Nat. Acad. Sci. (USA) [1982] 79:1979-1983.*
Arnon et al., *Targeted chemotherapy: drugs conjugated to anti-tumour antibodies*, Cancer Surveys 1(3):429-449 (1982).

* cited by examiner

*Primary Examiner*—Christina Chan
*Assistant Examiner*—F. Pierre VanderVegt
(74) *Attorney, Agent, or Firm*—DLA Piper US LLP

(57) ABSTRACT

A monoclonal antibody, 3E10, and active fragments thereof that selectively are transported in vivo to the nucleus of mammalian cells without cytotoxic effect are provided. The antibody and other molecules that bind to a variant of myosin IIb heavy chain found in the nucleus of skeletal muscle cells are useful as a non-viral delivery vector to target skeletal muscle in vivo. By contrast, in vitro the monoclonal antibody penetrates and is transported to the nucleus of multiple cell lines derived from different tissue types and can be used in screening tests to identify molecules that modulate growth of cells, such as cancer cells. Non-cytotoxic vectors for delivering a drug, polynucleotide or polypeptide selectively to skeletal muscle cells are also provided.

10 Claims, 5 Drawing Sheets

FIGURE 1A. Design of Constructs

SP-Vk    Linker    VH    p53 peptide

FIGURE 1B. PCR Primers

Primer     Nucleotide Sequence (5'-3')

(for *pSG5*)
3E10-Fv-SP  5'-GAATTCATGGAGTCAGACACACTGCTG
    CTATGGGTG-3'(SEQ ID NO:14)
3E10-Fv-HI  5'-GGATCCATGATGATGATGATGATGGTC-3'
    (SEQ ID NO:15)
p53A-S      5'-GGATCCGCTCACTCCAGCCACCT-3'
    (SEQ ID NO:16)
p53A-AS     5'-AGATCTTCAGTCTGAGTCAGGCCC-3'
    (SEQ ID NO:17)
p53B-S      5'-GGATCCGAGCCAGGGGGGAGCA-3'
    SEQ ID NO:18)
p53B-AS     5'-AGATCTTCAGTCTGAGTCAGGCCC-3'
    (SEQ ID NO:19)
p53C-S      5'-GGATCCCTGAATGAGGCCTTGGAACT-3'
    (SEQ ID NO:20)
p53C-AS     5'-AGATCTTCAGTCTGAGTCAGGCCC-3'
    (SEQ ID NO:21)
p53N-S      5'-GGATCCGAGGAGCCGCAGTCAGAT-3'
    (SEQ ID NO:22)
p53N-AS     5'-AGATCTTCAAATATCGTCCGGGGACAG-3'
    (SEQ ID NO:23)

(for *pPICZαA*)
3E10-Fv-S   5'-GAATCCGACATTGTGCTGACACAGT-3'
    (SEQ ID NO:24)
3E10-Fv-AS  5'-CCGCGGTCAATGATGATGATGATG
    ATGGGAGAC-3'(SEQ ID NO:25)
3E10-Fvp53A-S  5'-GAATCCGACATTGTGCTGACACAGT-3'
    (SEQ ID NO:26)
3E10-Fvp53A-AS 5'-CCGCGGTCAGTCTGAGTCAGGCCC-3'
    (SEQ ID NO:27)
3E10-Fvp53N-S  5'-GAATCCGACATTGTGCTGACACAGT-3'
    (SEQ ID NO:28)
3E10-Fvp53N-AS 5'-CCGCGGTCAGTCTGAGTCAGGCCC-3'
    (SEQ ID NO:29)

FIGURE 1C. Plasmid Constructs

| Plasmid | Host p53 Peptide Plasmid | Insert |
|---|---|---|
| *pscFv* | *pSG5* | --- |
| *pscFvp53A* | *pSG5* | aa 364-393 |
| *pscFv-p53B* | *pSG5* | aa 358-393 |
| *pscFv-p53C* | *pSG5* | aa 344-393 |
| *pscFv-Mut-p53A*\* | *pSG5* | aa 364-393 |
| *pscFv-p53N* | *pSG5* | aa 2-49 |
| | | |
| *pscFv* | *pPICZαA* | |
| *pscFv-p53A* | *pPICZαA* | aa 364-393 |
| *pscFv-p53N* | *pPICZαA* | aa 2-49 |

\**pscFv-Mut-p53A* contains the mutation R95Q in mAb 3E10 VH that prevents mAb 3E10Fv from penetrating living cells.

MYOSIN HEAVY CHAIN IIb (Homo Sapiens)

```
   1 mqgtledqii sanplleafg naktvrndns srfgkfirih fgatgklasa dietylleks
  61 rvtfqlkaer syhifyqils nkkpelieml littnpydfa fvsqgeitvp siddqeelma
 121 tdsavdilgf tadekvaiyk ltgavmhygn mkfkqkqree qaepdgteva dkaayltsln
 181 sadllkslcy prvkvgnefv tkgqtvqqvy navgalakai yekmflwmvt rinqqldtkq
 241 prqyfigvld iagfeifdfn sleqlcinft neklqqffnh hmfvleqeey kkegiewefi
 301 dfgmdlaaci eliekpmgif sileeecmfp katdtsfknk lyeqhlgksn nfqkpkpakg
 361 kpeahfslvh yagtvdynia gwldknkdpl netvvglyqk samktlaflf sgaqtaeaeg
 421 gggkkggkkk gssfqtvsal frenlnklmt nlrsthphfv rciipnetkt pgamehelvl
 481 hqlrcngvle giricrkgfp srilyadfkq rykvlnasai pegqfidskk asekllgsie
 541 idhtqykfgh tkvffkagll qtleemrdek laqlitrtqa icrgflmrve frkmmerres
 601 ifciqynira fmnvkhwpwm klyfkikpll ksaetekema nmkeefektk eelakteakr
 661 keleekmvtl mqekndlqlq vqaeadalad aeercdqlik tkiqleakik evteraedee
 721 einaeltakk rkledecsel kkdiddlelt lakvekekha tenkvknlte emagldetia
 781 kltkekkalq eahqqtlddl qmeedkvntl tkaktkleqq vddlegsleq ekklcmdler
 841 akrklegdlk laqestmdte ndkqqlnekl kkkefemsnl qgkiedeqal aiqlqkkike
 901 lqarieelee eieaerasra kaekqrsdls releeiserl eeaggatsaq iemnkkreae
 961 fqkmrrdlee stlqheataa alrkkhadsv aelgeqidsl qrvkqkleke kselkmeind
1021 lasnmetvsk akanfekmcr tledqlseik tkeeeqqrli nelsaqkarl htesgefsrq
1081 ldekdamvsq lsrgkqaftq qieelkrqle eetkakstla halqsarhdc dllreqyeee
1141 qeakaelqrg mskansevaq wrtkyetdai qrteeleeak kklaqrlqda eehveavnsk
1201 caslektkqr lqnevedlmi dversnaaci aldkkqrnfd kvlaewkqky eetqaeleas
1261 qkesrslste lfkvknayee sldhletlkr enknlqqeis dlteqiaegg khihelekvk
1321 kqldheksel qtsleeaeas leheegkilr iqlelnqvks eidrkiaekd eeldqlkrnh
1381 lrvvesmqst ldaeirsrnd alrikkkmeg dlnemeiqln hanrqaaeal rnlrntqgil
1441 kdtqlhldda irgqddlkeq lamverranl mqaeveelra slertergrk maeqelldas
1501 ervqllhtqn tslintkkkl etdisqiqge medivqearn aeekakkait daammaeelk
1561 keqdtsahle rmkknmeqtv kdlqlrldea eqlalkggkk qiqklearvr eleseveseq
1621 khnveavkgl rkherrvkel tyqteedrkn ilrlqdlvdk lqtkvkaykr qaeeaeeqsn
1681 vnlakfrklq heleeakera diaesqvnkl rvksrevhtk visee
```

Figure 6

DELIVERY SYSTEM USING MAB 3E10 AND MUTANTS AND/OR FUNCTIONAL FRAGMENTS THEREOF

This application is a Continuation-in-Part Application of U.S. application Ser. No. 09/142,142, filed Nov. 9, 1998 now abandoned; which was the National Stage of International Application No. PCT/US97/03785 under 37 CFR § 371, filed Mar. 7, 1997 and relies for priority upon U.S. Provisional Application Ser. No. 60/013,297, filed Mar. 8, 1996.

This invention was made with Government support from the Department of Veterans Affairs. The Government has certain rights in this application.

FIELD OF THE INVENTION

The present invention relates to methods for the delivery of biologically active materials into cells, and compositions useful therefor.

BACKGROUND OF THE INVENTION

Autoantibodies to double stranded deoxyribose nucleic acid (dsDNA) are relatively specific for systemic lupus erythematosus (SLE) and are implicated in disease pathogenesis. Certain anti-DNA autoantibodies have been shown to penetrate cells and localize to the cell nucleus. Cellular penetration by anti-DNA antibodies was initially demonstrated in peripheral blood T-lymphocytes (see, for example, Okudaira, et al., in *Arthritis Rheum.* 30:669 (1987) and Alarcon-Segovia, et al., in *Clin. exp. Immunol.* 35:364 (1979)) and, subsequently, was shown to affect their function (see, for example, Okudaira, et al., supra, Alarcon-Segovia, et al., in *J. Immunol.* 122:1855 (1979), Alarcon-Segovia, et al., in *Clin. Immunol. Immunopath.* 23:22 (1982), Alarcon-Segovia and Llorente in *Clin. exp. Immunol.* 52:365 (1983), and Alarcon-Segovia, in *Clinics in Immunology and Allergy* 1:117 (1981)).

In some studies, antibody penetration was thought to be mediated by Fc receptors (see, for example, Llerena, et al., in *Immunology* 43:249 (1981) and Alarcon-Segovia, et al., in *Nature* 271:67 (1978)). For other anti-DNA antibodies, cellular penetration and translocation to the cell nucleus was thought to require the presence of DNA (see, for example, Okudaira, et al., supra). More recently, penetration of anti-DNA antibodies has been demonstrated in mesangial cells (Vlahakos, et al., in *T. Am. Soc. Nephrol.* 2(8):1345 (1992)). Anti-DNA antibodies have been shown to enter the nucleus of cultured mesangial and hepatoma cells in a time and temperature dependent manner (Yanase, et al., in *Lab. Invest.* 71:52 (1994).

There are multiple mechanisms by which anti-DNA antibodies are thought to penetrate cells. Indeed, different antibodies may use different pathways. Since some anti-DNA antibodies have been shown to bind membrane proteins cross reactive with DNA, these proteins may be instrumental in cellular penetration (see, for example, Brentjens and Andres in *Kidney International* 35:954 (1989), Raz, et al., *J. Immunol.* 142:3076 (1989), Madaio, et al., in *J. Immunol.* 138:2883 (1987), Faaber, et al., in *J. Clin. Invest.* 77:1824 (1986), Ben-Chetrit, et al., in *Clin. exp. Immunol.* 60:159 (1985), Jacob, et al., in *Proc. Natl. Acad. Sci. USA* 81:3843 (1984), Jacob, et al., in *Proc. Natl. Acad. Sci. USA* 86:4669.4669 (1989), Raz, et al., in *Eur. J. Immunol.* 23:383.383 (1993), and Jacob, et al., in *J. Clin. Invest.* 75:315 (1985)). In other cases, DNA binding proteins usually thought of as intracellular have been described in association with the membrane of some cells (see, for example, Bennett, et al., in *J. Clin. Invest.* 76:2182 (1985) and Refeneider, et al., in *Clin. Immunol. Immunopath.* 63:245 (1992)). Anti-DNA antibodies could form complexes with these proteins through their mutual binding to DNA.

For additional background information, see U.S. Pat. No. 4,812,397 and "DNA Mimics a Self-Protein That May Be a Target for Some Anti-DNA Antibodies in Systemic Lupus Erythematosus", *Journal Of Immunology*, pages 1987–1994 (Feb. 15, 1995), the contents of each of which are hereby incorporated by reference in their entirety.

Mutations in the p53 tumor suppressor protein are a frequent cause of cancer. Methods to regulate and restore the function of p53 are promising approaches to the treatment of cancer. Restoring p53 function by delivering functional p53 into cancer cells and delivering p53 peptides have been investigated in several studies. Various delivery vehicles have been used to deliver p53 and p53 peptides into cancer cells for restoration of p53 function. These include VP 22, a herpes simplex virus 1 protein (15,16), and the third alpha helix of Antennapedia homeodomain (8). The potential disadvantage of these vectors is that they are foreign proteins that may be immunogenic in humans.

In view of the availability of antibodies which are capable of penetrating cells, it would be desirable to selectively utilize such cell penetrating properties for the directed manipulation of biological materials.

BRIEF DESCRIPTION OF THE INVENTION

The invention overcomes these and other problems in the art by providing methods for transporting a biologically active molecule into the nucleus of a target cell in vitro. In the in vitro invention methods the biologically active molecule is combined with mAb 3E10 as produced by a hybridoma having ATCC accession number PTA 2439, or mutant or functional fragment thereof, and the target cell is contacted in vitro under suitable conditions with the resulting combination, thereby transporting the biologically active molecule into the nucleus of the target cell.

In another embodiment the invention provides in vivo methods for selectively transporting a biologically active molecule to the nucleus of skeletal muscle cells in a living subject. In the in vivo methods, the subject is administered a biologically active molecule combined with a transport molecule that specifically binds to the nuclear isoform of the heavy chain of myosin IIb, thereby selectively transporting the biologically active molecule into skeletal muscle cells of the subject.

In yet another embodiment, the invention provides vectors for selectively transporting a biologically active molecule into skeletal muscle cells contained in a mammalian subject. The invention vector comprises a transport molecule that, in a live subject, specifically binds to a nuclear isoform of myosin heavy chain IIb and a biologically active molecule chemically associated with the monoclonal antibody, or mutant or functional fragment thereof.

In still another embodiment, the invention provides antibodies that specifically bind to the newly discovered nuclear isoform of myosin IIb heavy chain and not to other isoforms of myosin IIb heavy chain.

DESCRIPTION OF THE FIGURES

FIG. 1A is a schematic representation of the plasmid constructs used in construction of fusion proteins encoding an scFv of mAb 3E10 and various polymers of the C-terminal region of p53 protein.

FIG. 1B shows the sense (S) and antisense (AS) nucleotide primers used for construction of the various plasmids illustrated in FIG. 1A and used in Example 8.

FIG. 1C shows the host plasmid and amino acid segments of p53 contained in the p53 Peptide insert in the various plasmids illustrated in FIG. 1A and used in Example 8.

FIG. 6 shows the amino acid sequence of a 200 kDa human skeletal muscle protein (SEQ ID NO: 13) identified as myosin IIb by Nano-LC/MS/MS. Underlining shows the 28 peptides identified by Nano-LC/MS/MS of rat skeletal muscle as identical with the human skeletal muscle protein.

DETAILED DESCRIPTION OF THE INVENTION

Figure 2:
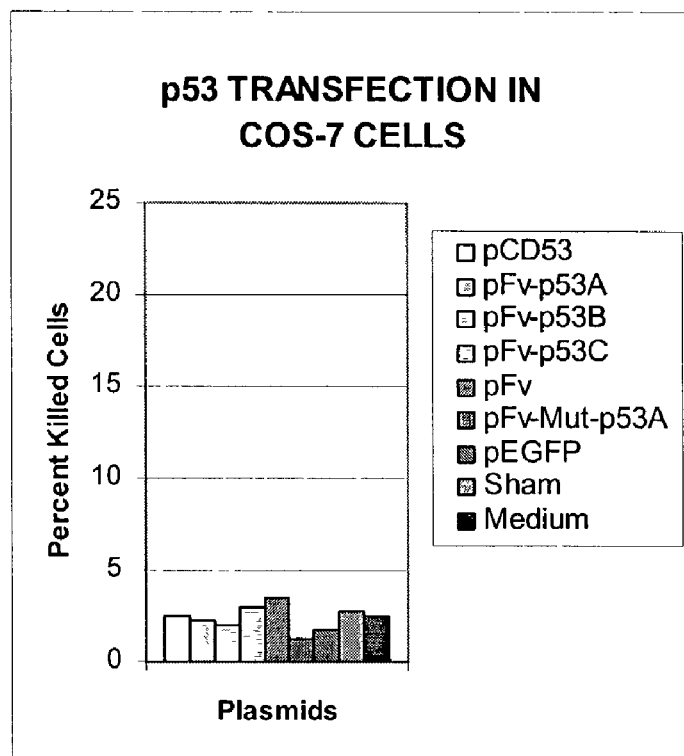
FIG. 2 is a graph showing cytotoxicity of p53 transfection from pscFv-p53A, B, and C transfected into COS-7 cells.

In accordance with the present invention, there are provided methods for the transport of biologically active molecules into a target cell. Invention methods comprise combining a biologically active molecule with mAb 3E10, or mutants or functional fragments thereof, and administering the resulting combination to said cell.

In accordance with another embodiment of the present invention, there are provided methods for the transport of biologically active molecules into a target cell, said method comprising: combining said biologically active molecule with a non-pathogenic monoclonal antibody, wherein said antibody promotes transport into said cell in an energy independent manner, and wherein said antibody is not anti-RNP, and administering the resulting combination to said cell.

Monoclonal antibodies (mAb) useful in the practice of the present invention, e.g., non-pathogenic monoclonal antibodies which promote transport into cells in an energy independent manner, and which are not anti-RNP antibodies, are capable of penetrating renal tubular epithelial cells in vivo and primary cultured neurons. Upon penetration, mAbs according to the invention (e.g., 3E10, as well as mutants and/or functional fragments thereof) localize in the cell nucleus.

In accordance with the present invention, it has been discovered that there is a class of monoclonal antibodies (e.g., mAb 3E10 and mutants and/or functional fragments thereof) which can be utilized to transport a wide variety of biologically important molecules into target cells, such as kidney cells, brain cells, ovarian cells, bone cells, and the like. Monoclonal antibody 3E10 is produced by a hybridoma 3E10 placed permanently on deposit with the American Type Culture Collection, 10801 University Blvd., Manassas, Va. 20110-2209, USA, on Aug. 31, 2000, according to the terms of the Budapest Treaty under ATCC accession number PTA-2439. Antibodies according to the invention (e.g., mAb 3E10 or mutants and/or functional fragments thereof) can be conjugated to the biological molecule of interest to form an antibody conjugate that is capable of being transported into the cell Upon entry into the cell, the antibody conjugate localizes in and around the cell nucleus. Antibody conjugates in accordance with the present invention may be used in the same manner as other conjugated delivery systems where an antibody or other targeting vehicle is conjugated to the biological molecule of interest to provide delivery to desired cells in the in vivo or in vitro environment.

Antibodies according to the invention (e.g., mAb 3E10 and mutants and/or functional fragments thereof) can be utilized to transport a wide variety of biologically active materials, e.g., nuclear transcription factors, enzymes, enzyme inhibitors, genes, and the like, to the cell nucleus for a variety of therapeutic effects. Pharmacologically active molecules including inorganic and organic molecules, pharmaceutical agents, drugs, peptides, proteins, genetic material, and the like, may be conjugated to antibodies according to the invention (e.g., mAb 3E10 and mutants and/or functional fragments thereof) for delivery thereof.

Naturally occurring antibodies are generally tetramers containing two light chains and two heavy chains. Experimentally, antibodies can be cleaved with the proteolytic enzyme papain, which causes each of the heavy chains to break, producing three separate subunits. The two units that consist of a light chain and a fragment of the heavy chain approximately equal in mass to the light chain are called the Fab fragments (i.e., the "antigen binding" fragments). The third unit, consisting of two equal segments of the heavy chain, is called the Fc fragment. The Fc fragment is typically not involved in antigen-antibody binding, but is important in later processes involved in ridding the body of the antigen.

As used herein, reference to mutants of mAb 3E10 includes variants of 3E10 which retain the same cell penetration characteristics as mAb 3E10, as well as variants modified by mutation to improve the utility thereof (e.g., improved ability to target specific cell types, improved ability to penetrate the cell membrane, improved ability to localize to the cellular DNA, and the like). Such mutants include variants wherein one or more conservative substitutions are introduced into the heavy chain, the light chain and/or the constant region(s) of the antibody.

As used herein, reference to functional fragments of mAb 3E 10 includes portions of 3E10 that retain the same cell penetration characteristics as mAb 3E10. Such functional fragments include fragments containing at least the antigen-binding portion of mAb 3E10.

As readily recognized by those of skill in the art, altered antibodies (e.g., chimeric, humanized, CDR-grafted, bifunctional, antibody polypeptide dimers (i.e., an association of two polypeptide chain components of an antibody, e.g., one arm of an antibody comprising a heavy chain and a light chain, or an Fab fragment comprising $V_L$, $V_H$, $C_L$ and $C_H1$ antibody domains, or an Fv fragment comprising a $V_L$ domain and a $V_H$ domain), single chain antibodies (e.g., an scFv (i.e., single chain Fv) fragment comprising a $V_L$ domain linked to a $V_H$ domain by a linker, and the like) can also be produced by methods well known in the art. Such antibodies can also be produced by hybridoma, chemical synthesis or recombinant methods described, for example, in (Sambrook et al., *Molecular Cloning: A Laboratory Manual* 2d Ed. (Cold Spring Harbor Laboratory, 1989); incorporated herein by reference and Harlow and Lane, *Antibodies: A Laboratory Manual* (Cold Spring Harbor Laboratory 1988), which is incorporated herein by reference). Both anti-peptide and anti-fusion protein antibodies can be used (see, for example, Bahouth et al., *Trends Pharmacol. Sci.* 12:338 (1991); Ausubel et al., *Current Protocols in Molecular Biology* (John Wiley and Sons, NY 1989) which are incorporated herein by reference).

A presently preferred mutant contemplated for use in the practice of the present invention is a mAb 3E10 VH mutant involving a single change of the aspartic acid residue at position 31 to asparagine (3E10-31). The preparation of this mutant and a demonstration of its cell penetration ability is set forth in Example 5. This particular mAb 3E10 mutant is especially well suited for delivery of biological molecules to kidney and brain cells. Other 3E10 mutants and/or functional fragments thereof may be used to provide targeting of biological molecules. A wide variety of mutants and/or functional fragments thereof are possible provided that they exhibit substantially the same cell penetration characteristics as mAb 3E10 and 3E10-31 after conjugation to a selected biological agent for delivery.

MAb 3E10 heavy or light chains can be produced as fusion proteins with a variety of biologically active materials, e.g., nuclear transcription factors, enzymes, enzyme inhibitors, and the like, thereby enabling the transport of these proteins into the cell nucleus of target cells. In addition, mAb 3E10 can be produced in the form of a fusion protein with other proteins that bind DNA (such as, for example, poly-L-lysine). The poly-L-lysine fusion protein with mAb 3E10 would bind DNA (e.g., plasmids containing genes of interest) and transport the DNA into the nucleus of target cells.

Fusion proteins can be designed to place the protein of interest at the amino or carboxy terminus of either the antibody heavy or light chain. Since the antigen binding fragments (Fab's) of mAb 3E 10 have been shown to penetrate cells and localize in the nucleus, the entire heavy chain is not required. Therefore, potential configurations include the use of truncated portions of the heavy and light chain with or without spacer sequences as needed to maintain the functional integrity of the attached protein.

As an alternative to producing fusion proteins as described hereinabove, a universal carrier system can be devised. For example, various proteins or DNA can be conjugated to a common carrier such as protein A, poly-L-lysine, hex-histidine, and the like. The conjugated carrier will then form a complex with antibody according to the invention. A small portion of the carrier molecule that is responsible for binding immunoglobulin could be used as the carrier. Other similar configurations include design of carriers that interact with proteins engineered into the antibody heavy or light chain.

The mode of delivery chosen for administration of antibody conjugates according to the present invention to a live subject, such as a human patient or mammalian animal, will depend in large part on the particular biological molecule present in the conjugate and the target cells. In general, the same dosages and administration routes used to administer the biological molecule alone will also be used as the starting point for the antibody conjugate. However, it is preferred that smaller doses be used initially due to the expected increase in cellular penetration of the biological molecule. The actual final dosage for a given route of administration is easily determined by routine experimentation. In general the same procedures and protocols that have been previously used for other antibody-based targeting conjugates (e.g., parenterally, intravenous, intrathecal, and the like) are also suitable for the antibody conjugates of the present invention.

Many anti-DNA antibodies can penetrate several types of cells and localize to the cell nucleus. Recent work indicates that cellular penetration requires complexes of antibody and DNA. MAb 3E10 can penetrate many different types of cell lines in tissue culture. In contrast, mAb 3E10 may be restricted in the cells it can bind and penetrate in vivo, where there is an absence of free DNA to facilitate its penetration. It appears that the penetration of mAb 3E10 into kidney cells in vivo occurs by a different mechanism by which certain antibodies can penetrate cells and localize to the cell nucleus. The use of mAb 3E10 to penetrate kidney cells and brain cells involves a mechanism which is not common to other anti-DNA antibodies which require the presence of DNA or antibody Fc binding.

Many different autoantibodies have been shown to penetrate cells, including antibodies to RNP (see, for example, Alarcon-Segovia et al. (1978) supra, Ma et al., in *Clin. exp. Immunol.* 93:396 (1993) and Galoppin and *J. Invest. Dermatol.* 76:264 (1981)), RNA (see, for example, Varesio, et al., in *Cancer Res.* 35:3558 (1975)), Ro (see, for example, Lee, et al., in *Arthritis Rheum.* 29:782 (1986)), Proteinase 3 (see, for example, Csernok, et al., in *Adv. Exp. Med. Biol.* 336:45 (1993)), ribosomal protein P (see, for example, Reichlin, et al., in *J. Clin. Invest.* 93:443 (1994) and Koren, et al., in *J. Immunol.* 154:4857 (1995)), lymphocytes (see, for example, Okudaira, et al., in *J. Clin. Invest.* 69:1026 (1982)), synaptosomes (see, for example, Fabian in *Neurology* 38:1775 (1988)), and neurons (see, for example, Dalmau, et al., in *Neurology* 41:1757 (1991) and Hormigo and Lieberman in *J. Neuroizamunol.* 55:205 (1994)), and some have been shown to localize in the cell nucleus. Antibodies to ribosomal protein P have been shown to penetrate pig renal cells, localize to the nucleus, and induce cell injury (see, for example, Reichlin et al., supra and Koren et al., supra), but the presence of DNA was not required.

The requirement for free DNA and the role of Fc binding for cellular penetration appears to be different for different antibodies, but the antibodies studied appear to have distinct specificities for binding antigen, and they target different cell types. Therefore, multiple mechanisms may be operative in cellular penetration and nuclear localization. In preliminary studies to determine the mechanisms for cellular penetration and nuclear localization of mAb 3E10, DNAse treatment and Fc blocking experiments were difficult to reproduce, indicating the complexity and potential artifacts involved in these procedures. Therefore, it was decided to produce mutants of mAb 3E10 variable heavy (VH) region and variable light (Vk for "variable kappa") region to definitively establish the relationship between antigen binding specificity and cellular penetration. The requirement for Fe binding and multivalent binding for cellular penetration was approached by producing molecular Fabs that are free of any contamination by undigested antibody or Fc fragments present in Fab prepared by enzyme digestion.

Monoclonal antibody 3E10 has recently been shown to cross react with a newly identified extracellular matrix protein, HP8/HEVIN (see Zack et al., in *Journal of Immunology* 154:1987–1994 (Feb. 15, 1995)). However, the present studies indicate that HP8/HEVIN is not involved in the penetration of mAb 3E10 into COS-7 or 3T3 cells. Indeed, it has been unequivocally shown that cellular penetration by mAb 3E10 correlates with DNA binding but is independent of Fc binding. Moreover, multivalent binding is not required. These results suggest that cellular penetration of mAb 3E 10 may occur through the formation of complexes containing antibody and DNA, but the possibility that mAb 3E10 bound to a membrane determinant that precisely resembles DNA cannot be excluded. Furthermore, the cell lines studied are penetrated by other (but not all) anti-DNA autoantibodies, suggesting a DNA dependent mechanism of penetration that may not reflect the specificity of binding and internalization of mAb 3E10 to renal tubular cells in vivo.

In addition to cellular penetration by anti-DNA antibodies, antineuronal antibodies have been shown to penetrate neurons, and the binding of intracellular targets has been proposed as a mechanism of disease pathogenesis (see, for example, Fabian in *Neurology* 40:419 (1990)). Moreover, a non-immunoglobulin protein has been shown to penetrate neurons and translocate to the nucleus. A 60 amino acid polypeptide corresponding to the homeodomain of the *Drosophila* protein Antennapedia was recently shown to penetrate neural cells, translocate to the cell nucleus, bind DNA, and regulate neural morphogenesis (see, for example, Joliot, et al., in *Proc. Natl. Acad. Sci. USA* 88:1864 (1991), La Roux, et al., in *Proc. Natl. Acad. Sci. USA* 90:9120 (1993), Bloch-Gallego, et al., in *The Journal of Cell Biology* 120:485 (1993) and Derossi, et al., in *J. Biol. Chem.* 269: 10444 (1994)). Recovery of intact peptide suggests that targeting was not to the lysosomal compartment. Sequence homology between the Antennapedia homeodomain peptide and mAb 3E10 VH or Vk is not apparent.

The mechanism for the nuclear transport of anti-DNA antibodies remains unknown, but it has been suggested that the anti-DNA antibodies might be transported to the nucleus of cells as a result of arginine-rich sequences similar to the nuclear transport signals associated with nuclear transcription factors and other proteins (see, for example, Hanover in *The FASEB Journal* 6:2288 (1992)). Although the amino acid sequences of mAb 3E10 VH and Vk do not show linear sequences similar to known nuclear transport signals, these signals are quite diverse and may not be easily recognized. A novel binding domain of mAb 3E10 VH that is shared only by certain anti-DNA antibodies and is composed of conserved amino acid sequences in FR1 and FR3 has been described (see, for example, Zack, et al., in *Immunology and Cellular Biology* 72:513 (1994)). These regions have many arginine and lysine residues that could form a nuclear transport signal by their proximity in the three dimensional structure. Therefore, mAb 3E10 has several potential determinants that could serve as nuclear transport signals. These may bind other proteins (such as the recently described hSRP1α) that act as functional receptors for some nuclear localization sequences and assist in transport across nuclear membranes (see, for example, Weis, et al., in *Science* 268:1049 (1995)). Alternatively, in some cases, carbohydrates are also used as nuclear transport signals (see, for example, Duverger, et al., in *Exp. Cell Res.* 207:197 (1993)). Glycosylation of the variable regions of the heavy or light chains could serve as a nuclear transport signal.

To assess the mechanism of nuclear transport of mAb 3E 10, heavy and light chain cDNA devoid of signal peptide sequences were transfected into COS-7 cells. The engineered antibody was expressed in the cytoplasm and translocated to the cell nucleus (see, for example, Biocca, et al., in *EMBO* 9 (1):101 (1990)). In contrast, mAb 3E10 was not translocated from the cytoplasm to the nucleus. Therefore, either the primary sequence alone is unable to initiate transfer of the antibody into the nucleus, or transport to the nucleus utilizes a pathway initiated by binding to the cell membrane. In either case, the mechanism for the nuclear localization of mAb 3E10 may be different than the transport mechanism used for cytoplasmic proteins such as nuclear transcription factors. Since mAb 3E10 was not found in the nucleus of COS-7 cells that produced and secreted antibody, the antibody secretary and nuclear transport pathways must also be separate.

The present invention demonstrates the usefulness of specific antibodies for the introduction of biologically active molecules into cells, as well as the usefulness of producing molecular mutants and/or functional fragments of such autoantibodies in studying the cellular pathways of autoantibody penetration and nuclear localization.

It has been discovered that a single mutation in VH of monoclonal antibody 3E10 enhanced penetration to permit detection of nuclear localization at concentrations of only a few ng/ml. An scFv fragment was shown to be as effective as whole antibody in penetrating living cells, and cellular penetration and nuclear localization occurred in the absence of cellular toxicity. It has previously been shown that a complex of whole mAb 3E10 and catalase delivered neuroprotective amounts of catalase into primary neurons (R. H. Weisbart et al. *J. Immunol.* 164:6020, 2000). The antibody was now tested as a transport vehicle for restoration of p53 function in cancer cells using a polynucleotide encoding a fusion protein.

SW480 cells that contain two mutations in p53, His-273/Ser-309 were studied because they were shown by others to be sensitive to killing by p53 peptides. In the experiments described in Example 8, the results show that only a 30-mer C-terminal peptide of p53 produced significant cytotoxicity in SW480 cells, but not in COS-7 and CHO cells containing wild type p53. Cytotoxicity was modest even though the fusion protein was shown to penetrate all of the cells. However, the amount of fusion protein that penetrated cells was variable. Longer C-terminal peptides consisting of 36 and 50 C-terminal amino acids did not produce significant cytotoxicity.

Transcriptional activation of p53 was examined with the use of a CAT reporter attached to a consensus DNA binding domain for p53. Transfection of SW480 cells with pscFv-p53A and incubation of SW480 cells with scFv-p53A polypeptide did not increase the production of CAT, indicating that cytotoxicity of the p53A peptide was not due to restoration of p53 transcriptional activation. This finding is consistent with a recent report challenging the concept that the C-terminal of p53 is a negative regulatory domain.

The 30-mer C-terminal peptide of p53 expressed from a fusion protein containing the 3E10 monoclonal scFv fragment as nuclear delivery protein was cytotoxic for SW480 cells in vitro, but not as a result of restoring transcriptional activation of p53. Furthermore, peptide-induced cytotoxicity was modest. These results may differ from other studies of p53 peptide because a different nuclear delivery system was used and different C-terminal peptides of p53 were used. In spite of the apparent limitations of p53 peptide-induced cytotoxicity in SW480 cells in these studies, efficacy of the 3E10 monoclonal scFv fragment as a nuclear delivery vehicle in cancer cells in vitro is fully demonstrated by the data shown in Example 8 below.

In vitro, mAb 3E10 penetrates multiple types of living cells and localizes in the cell nucleus. scFv fragments of mAb 3E10 were produced and shown to penetrate living cells comparable to whole antibody. When injected intravenously into a mouse, however, mAb 3E10 scFv fragments were found localized primarily in the nucleus of skeletal muscle cells. To identify proteins responsible for cellular penetration and nuclear localization, the antibody was used to probe Western blots containing proteins derived from nuclear and cytoplasmic lysates of different tissues. The antibody bound a 200 kDa protein found primarily in nuclear lysates of skeletal muscle cells. The specificity of antigen binding was consistent with the specificity of tissue penetration in vivo. The protein antigen was identified as myosin IIb by direct amino acid sequence analysis of the 200 kDa protein purified by antibody affinity chromatography and by the absence of the protein antigen in mice null for myosin IIb. The nuclear location of myosin IIb reactive with mAb 3E10 was confirmed microscopically in fixed muscle samples, indicating the presence of a nuclear isoform of myosin IIb not previously described.

Studies were conducted with lysates from multiple cell lines derived from different tissues in which mAb 3E10 penetrates. However, in these cell lines the studies failed to elucidate a protein responsible for transport of the antibody into cells grown in tissue culture. Therefore, it appears that the mechanisms for cellular penetration and nuclear localization of antibody into cell lines in vitro may be different than for antibody transport into skeletal muscle in vivo.

A variety of mechanisms responsible for autoantibody transport into cell lines have been implicated, including requirement for Fc receptors, and antibody binding to brush border myosin I (Alarcon-Segovia et al., 1978; Yanase et al., 1997). As shown in this study, mAb 3E10 did not bind myosin I, and scFv fragments devoid of the Fc region were able to penetrate living cells. It appears, therefore, that different antibodies may penetrate living cells by different mechanisms. It is possible that dsDNA may be a molecular mimic of diverse protein epitopes, some of which are molecular motors or messenger molecules.

Anti-DNA antibodies are only one small group of proteins identified that penetrate living cells. It is well known that a series of small protein transduction domains cross biological membranes independently of transporters or specific receptors, including a nine amino acid peptide of the HIV transactivation factor, TAT, VP22, a herpes simplex virus 1 protein, and the third alpha helix of Antennapedia homeodomain. It seems less likely that antibody molecules cross biological membranes through similar transduction domains because of their large size. Moreover, in contrast to small protein transduction domains that penetrate all cells, different antibodies demonstrate different tissue and cell specificities. Therefore, the motor function of myosin IIb is a more likely candidate for the transport of mAb 3E10 into skeletal muscle cells. However, further studies are required to define the precise pathway by which myosin IIb facilitates antibody transport into skeletal muscle cells.

Antibodies that penetrate living cells are frequently toxic or injurious and may explain some of the pathologic manifestations of the autoimmune diseases in which they are found. In contrast, mAb 3E10 shows no harm to cells that it penetrates in tissue culture (Weisbart et al., 1998). Moreover, studies in vitro have shown that mAb 3E10 and scFv fragments of mAb 3E10 can transport relatively large proteins, such as catalase, into the nucleus of cells in tissue culture (Weisbart et al., 2000). Despite this result of the in vitro studies, it has now surprisingly been discovered that in vivo (i.e., in live mammals, for example murine animals and humans), mAb 3E10 and functional fragments thereof selectively penetrate in living animals (i.e., in vivo) to the nucleus only of skeletal muscle cells. This surprising finding indicates that both the 3E10 antibody and the scFv fragment disclosed herein (and the elements of its transport pathway) are useful in the design of therapeutic, non-viral delivery vectors to selectively target skeletal muscle in vivo. Such studies also show that other molecules, such as other antibodies, that will specifically and selectively bind to the newly discovered nuclear isoform of myosin IIb heavy chain (i.e., that do not bind to other isoforms of myosin IIb heavy chain) can be used as the transport molecule in an invention vector to selectively deliver biologically active molecules, such as therapeutic molecules, proteins and polynucleotides encoding biologically active molecules, to skeletal muscle in vivo.

Although myosin IIb is primarily a cytoplasmic protein, studies described in Example 9 below identify a heretofore unknown variant of myosin IIb (SEQ ID NO: 13) that is localized in the nucleus of skeletal muscle cells. The structure of the isoform of myosin IIb reactive with mAb 3E10 remains to be elucidated, but may be due to a post-translational modification of the molecule. It has now been discovered that this newly recognized isoform of myosin IIb selectively facilitates the transport of mAb 3E 10 into the nucleus of skeletal muscle cells.

Therefore, based on the studies described herein, in one embodiment, the invention provides methods for transporting a biologically active molecule into a target cell in vitro by combining the biologically active molecule with mAb 3E10 as produced by a hybridoma having ATCC accession number PTA 2439, or mutant or functional fragment thereof, and contacting the target cell in vitro under suitable conditions with the resulting combination, for example by culturing the target cells under growth conditions in the presence of the combination, for example as described in the Examples herein. By this method, the biologically active molecule is transported into the nucleus of the target cell. This embodiment of the invention is particularly useful as a research tool to discover molecules that will modulate the growth of cells in culture. For example, the invention method can be used as a screening tool to identify molecules that will inhibit growth of cancer cells in culture. Those molecules that pass this screening test can then be further utilized in additional screening tests in vivo to determine such attributes of selected molecules as in vivo function, side effects and safety.

For use in the invention methods, in addition to conjugating the antibody to the biologically active molecule, the latter can be attached to or associated with mAb 3E10 by any method known in the art. For example an scFv fragment of mAb 3E10, as described herein, can be expressed in a host cell as a fusion protein additionally containing a biologically active polypeptide for screening. Alternatively, the monoclonal antibody, or active fragment thereof, can be chemically linked to a polypeptide by a peptide bond or by a chemical or peptide linker molecule of the type well known in the art. Method for attaching a drug or other small molecule pharmaceutical to an antibody fragment are well known and include bifunctional chemical linkers such as N-succinimidyl (4-iodoacetyl)-aminobenzoate; sulfosuccinimidyl(4-iodoacetyl)-aminobenzoate; 4-succinimidyl-oxycarbonyl-∀-(2-pyridyldithio) toluene; sulfosuccinimidyl-6-[α-methyl-∀-(pyridyldithiol)-toluamido] hexanoate; N-succinimidyl-3-(-2-pyridyldithio)-proprionate; succinimidyl-6-[3 (-(-2-pyridyldithio)-proprionamido] hexanoate; sulfosuccinimidyl-6-[3 (-(-2-pyridyldithio)-propionamido] hexanoate; 3-(2-pyridyldithio)-propionyl hydrazide, Ellman's reagent, dichlorotriazinic acid, S-(2-thiopyridyl)-L-cysteine, and the like. Further bifunctional linking molecules are disclosed in U.S. Pat. Nos. 5,349,066, 5,618,528, 4,569, 789, 4,952,394, and 5,137,877, each of which is incorporated herein by reference in its entirety.

In yet another embodiment the invention provides methods for selectively transporting a biologically active molecule to the nucleus of skeletal muscle cells in a living subject by administering to the subject the biologically active molecule associated with a transport molecule that specifically and selectively binds to the nuclear isoform of the heavy chain of myosin IIb, thereby selectively transporting the biologically active molecule into the nucleus of skeletal muscle cells of the subject (i.e., the transport molecule does not bind to other isoforms of myosin IIb heavy chain). Therefore specific and selective binding of the transport molecule to the nuclear isoform of the heavy chain of myosin IIb in the skeletal muscle cells transports the associated biologically active molecule selectively into skeletal muscle cells. For example, the transport molecule can be either whole antibody or functional fragment or mutant thereof that specifically binds to the nuclear isoform of the heavy chain of myosin IIb in the skeletal muscle cells and not to other isoforms of myosin IIb. A presently preferred antibody for use as the transport molecule is mAb 3E10, or mutant or functional fragment thereof. The conjugate of the functional fragment and biologically active molecule can be a fusion protein expressed from a host cell, for example an scFv fragment comprising the variable region of the heavy chain (VH) and variable region of the kappa light chain (Vκ) of mAb 3E10. For increased expression in the polynucleotide from which the scFv is expressed, the nucleic acids encoding the chains of mAb E310 are placed in reverse order with the Vκ cDNA being placed 5' of VH.

A polynucleotide, such as one encoding a therapeutic protein, can also be selectively transfected into skeletal muscle cells by the invention vector by chemically bonding the polynucleotide to a transport molecule as disclosed herein, such as mAb 3E10 of a function fragment thereof, for example an scFv. Polynucleotides delivered into skeletal muscle cells in the subject using the invention vectors become stably integrated into the nucleus of the skeletal muscle cells. If the polynuleotide contains a gene rather than a regulatory molecule, the gene can be selectively expressed in the skeletal muscle cells of the subject.

In still another embodiment, the invention provides vectors for selectively transporting a biologically active molecule into skeletal muscle cells contained in a mammalian subject. The invention vectors comprise a transport molecule, for example a monoclonal antibody, or mutant or functional fragment thereof, that, in a live subject, specifically and selectively binds to a nuclear isoform of myosin heavy chain IIb and a biologically active molecule chemically associated with the transport molecule. A presently preferred candidate monoclonal antibody for use in the invention vectors is mAb 3E10 as produced by a hybridoma having ATCC accession number PTA 2439, or mutant or functional fragment thereof. In one embodiment, the functional antibody fragment in the invention vector is an scFv fragment. If the biologically active molecule is a polypeptide, such as a therapeutic polypeptide, the scFv fragment and the biologically active polypeptide can be contained in a fusion protein. Alternatively a functional fragment can be used to delivery a gene encoding a therapeutic protein or functional fragment thereof. A preferred functional fragment is comprises the VH and Vκ of mAb E310 and may optionally further comprise the signal peptide of the Vκ. Such an scFv fragment is conveniently expressed from a polynucleotide having the nucleic acid encoding the Vκ 5' of the nucleic acid encoding the VH.

For expression of polynucleotides encoding an invention vector, such as one comprising an scFv, the polynucleotide can be ligated into an expression construct, with each expression construct comprising a vector containing one or more of the polynucleotides. The vector may further comprise expression regulatory sequences operably associated with the polynucleotide that can control and regulate the production in an appropriate host cell of a polypeptide(s) encoded by the polynucleotide.

In still another embodiment, the invention provides antibodies that specifically bind to the newly discovered nuclear isoform of myosin IIb heavy chain and not to other isoforms of myosin IIb heavy chain. Antibodies raised against myosin IIb heavy chain that bind selectively to the nuclear isoform of the protein can be prepared by those of skill in the art using conventional methods as disclosed herein and are known in the art, with the additional step that antibodies that bind specifically and selectively to the nuclear isoform of myosin IIb heavy chain are separated from antibodies that bind to other isoforms of myosin IIb heavy chain by attaching the nuclear isoform in its native 3-D configuration to a separation column as is known in the art and obtaining from the selection column only the antibodies that selectively bind to the nuclear isoform of the myosin IIb heavy chain. In addition to antibodies, antibody fragments and mutants of either, other transport molecules useful in the invention methods and vectors can be obtained in a similar fashion, i.e., by separating out, for example by means of a separation column, the putative transport molecules that bind to the nuclear isoform of myosin IIb heavy chain in its native 3-D configuration and do not bind to other isoforms of myosin IIb heavy chain.

Vectors suitable for use in preparation of polypeptides such as the invention antibody-containing vector include those selected from baculovirus, phage, plasmid, phagemid, cosmid, fosmid, bacterial artificial chromosome, viral DNA, P1-based artificial chromosome, yeast plasmid, and yeast artificial chromosome. For example, the viral DNA vector can be selected from vaccinia, adenovirus, foul pox virus, pseudorabies and a derivative of SV40. Suitable bacterial vectors for use in practice of the invention methods include pQE70, pQE60, pQE-9, pBLUESCRIPT SK, pBLUESCRIPT KS, pTRC99a, pKK223-3, pDR540, PAC and pRIT2T. Suitable eukaryotic vectors for use in practice of the invention methods include pWLNEO, pXTI, pSG5, pSVK3, pBPV, pMSG, and pSVLSV40. Suitable eukaryotic vectors for use in practice of the invention methods include pWLNEO, pXTI, pSG5, pSVK3, pBPV, pMSG, and pSVLSV40.

Those of skill in the art can select a suitable regulatory region to be included in such a vector, for example from lacI, lacZ, T3, T7, apt, lambda PR, PL, trp, CMV immediate early, HSV thymidine kinase, early and late SV40, retroviral LTR, and mouse metallothionein-I regulatory regions.

Host cells in which the vectors containing the polynucleotides can be expressed include a bacterial cell, a eukaryotic cell, a yeast cell, an insect cell, or a plant cell. For example, E. coli, Bacillus, Streptomyces, Salmonella typhimurium, Drosophila S2, Spodoptera SJ9, CHO, COS (e.g. COS-7), or Bowes melanoma cells are all suitable host cells for use in practice of the invention methods.

The invention will now be described in greater detail by reference to the following non-limiting examples.

EXAMPLE 1

Monoclonal Antibodies mAbs 3E10, 5C6, and 4H2 are IgG2a anti-dsDNA antibodies which were produced from spleen cells of MRL-mpj/lpr mice by fusion with cells from the FOX-NY cell line as previously described (see Weisbart, et al., in *J. Immunol.* 144:2653 (1990)). mAb PP102 (Chemicon International, Temecula, Calif.), a murine IgG2a antibody that does not bind DNA, was used as a non-anti-DNA antibody isotype-matched control.

EXAMPLE 2

Monoclonal anti-DNA Antibody Binding in Vitro to Tissues of Human Organs

The monoclonal antibodies were purified from ascites by affinity chromatography using protein A-Sepharose and tested for binding kidney. mAb 3E10 was also tested for the ability to bind tissues from 19 other human organs, including blood vessels, nerve trunks, liver, connective tissues, lung, pancreas, gut, cardiac muscle, striated muscle, spleen, ovary, testis, thyroid, skin, eye, adrenal, brain, pituitary, and bone. Binding of monoclonal antibodies was detected with peroxidase conjugated affinity purified rabbit antibodies specific for mouse IgG Fc as previously described (see Taylor and Lote in *Immunomicroscopy: A diagnostic tool for the surgical pathologist*. Saunders, W. B., Philadelphia (1994)).

mAb 3E10 Binds Human Renal Tubular Cells in Vitro

Three anti-dsDNA antibodies, i.e., mAbs 3E10, 5C6, and 4H2, were studied in vitro for binding tissue from fixed normal human kidney. All of the antibodies bound cell nuclei consistent with their anti-DNA reactivity. Thus, low magnification of renal tubular cells incubated with mAb 3E 10 shows reactivity with renal tubular cell membranes and nuclei. Higher magnification emphasizes linear binding of mAb 3E10 to membranes of renal tubular cells. Only mAb 3E10 is seen to bind the cell surface of renal tubular cells.

The cell surface binding appeared consistent with binding the cell membrane. While mAb 3E 10 bound tubular cells in five of five normal human kidneys studied, there was some variability in the intensity of staining. The results of incubating another anti-DNA antibody, mAb 5C6, with normal human kidney tubules shows binding to nuclei, but absence of binding to tubular cell membranes. The anti-DNA reactivity of mAb 5C6 is evident by the nuclear staining. However, in contrast to mAb 3E10, mAb 5C6 did not bind to renal tubular membranes.

Similarly, mAb 4H2 did not bind renal tubular membranes. None of the monoclonal anti-dsDNA antibodies were observed to bind antigens in renal glomeruli.

The specificity of binding of mAb 3E10 to kidney tubules was evaluated by studying its binding to tissues from other human organs. mAb 3E10 did not bind membranes or cytoplasmic antigens in tissues from multiple other organs, including blood vessels, nerve trunks, liver, connective tissues, lung, pancreas, gut, cardiac muscle, striated muscle, spleen, testis, thyroid, skin, eye, adrenal, pituitary, and bone. However, results of binding ovary and brain were inconclusive.

EXAMPLE 3

Monoclonal anti-DNA Antibody Binding in Vivo to Tissues of Normal BALB/c Mice

Normal BALB/c mice were primed with pristane and injected intraperitoneally with 2×10$^7$ hybridoma cells. After two weeks, the animals developed ascites containing antibodies with anti-dsDNA reactivity. Heart, liver, and kidney tissues were obtained and preserved in liquid nitrogen for studies of tissue histology. Binding of the anti-DNA antibodies to tissues was detected with peroxidase-conjugated affinity-purified rabbit antibodies specific for mouse IgG Fc as previously described (see Taylor and Lote supra).

mAb 3E10 Binds Murine Renal Tubular Cells in Vivo

Thus, to determine if mAb 3E10 was reactive with mouse renal tubular cells in vivo, kidneys were examined from normal BALB/c mice two weeks after intraperitoneal injection with 3E10 cells to establish ascites containing high concentrations of mAb 3E10. mAb 3E10 did not localize in the membrane, cytoplasm, or nuclei of liver, cardiac muscle, or renal glomerular cells. Examination of renal tubular cells, however, showed nuclear staining, indicating that mAb 3E10 was selectively internalized and transported to the nucleus in renal tubular cells in vivo. The same results were observed in three of three BALB/c mice with ascites from 3E10 cells. In contrast to sections of dead, fixed tissue incubated with mAb 3E10 in vitro where the nuclei were exposed to the antibody, living, intact kidney cells in BALB/c mice would not be expected to contain intracellular antibody unless the antibody bound to cell membranes and entered the cells. In view of the fact that mAb 3E10 penetrated live renal tubular cells, it is likely that the cell surface staining observed in fixed dead cells could be attributed to binding the cell membrane.

The renal tubular cells from BALB/C mice with 3E10 ascites were examined in microscopic sections stained with either hematoxylin/eosin or Periodic Acid Schiff reagents. No significant abnormalities were observed.

The selective penetration of mAb 3E10 into intact renal tubular cells suggests that internalization was the result of specific antibody binding. Moreover, mAb 3E10 appears to have been transported across the nuclear membrane to localize in the nucleus in living renal tubular cells. In contrast, none of three BALB/c mice with ascites containing mAb 4H2 anti-dsDNA antibody showed binding of mAb 4H2 to liver, cardiac muscle or kidney. Comparable amounts of mAb 3E10 (0.8 mg/ml) and mAb 4H2 (1.0 mg/ml) were present in ascites used in these experiments. In contrast to mAb 4H2, mAb 3E10 enters the tubular cells and binds the cell nuclei.

These results suggest that mAb 3E10 is reactive with a membrane antigen on renal tubular cells in mouse as well as human kidney, and that the anti-kidney antibody binds renal tubular cells and is internalized and transported to the nucleus in vivo.

EXAMPLE 4

Cell Lines

MDCK dog kidney cells were kindly provided by Dr. Mostov, University of California, San Francisco, Calif. (see Apodaca, et al., in *The Journal of Cell Biology* 125:67 (1994)). Other cell lines, including 293 human embryonal kidney cells, COS-7 monkey kidney cells, NIH 3T3 cells, HT-29 colon cancer cells and LS 174T colon cancer cells were obtained from the American Type Culture Collection (ATCC, Rockville, Mass.). The cells were grown overnight in 96 or 48 well tissue culture plates in Dulbecco's modified Eagle media (DMEM, GIBCO BRL Life Technologies, Inc., Gaithersburg, Md.) in the presence of 10% horse serum (293 cells) or fetal calf serum (remaining cell lines) at 37° C., 5% $CO_2$, and humidified atmosphere.

After one day all media were aspirated and replaced with fresh media containing monoclonal antibodies. In preliminary studies, it was determined that a 10 μg/ml concentration of purified monoclonal antibody was required to demonstrate binding to cells. In contrast, hybridoma supernatants (diluted 1:1 with fresh medium) containing 0.5 μg/ml were as effective as purified antibodies, so subsequent studies were done with purified antibodies (10 μg/ml) or hybridoma supernatants.

Cells were incubated with antibody for 1 to 2 hours and washed three times in Hanks Buffered Salt Solution and phosphate buffered saline (PBS). The cells were then fixed with 70% ethanol for 10 to 20 minutes and washed again multiple times in PBS. The cells were then incubated for 1 hour with alkaline phosphatase conjugated goat anti-mouse antibodies specific for binding IgG2a. The cells were washed three times in PBS and stained with nitro blue tetrazolium chloride/5-bromo-4-chloro-3indolylphosphate p-toluidine salt (NBT/BCIP) in color development solution containing levamisole.

mAb 3E10Penetrates Living Kidney Cells in Tissue Culture and is Translocated to the Nucleus Several cell lines were examined for binding mAb 3E10. Kidney cell lines from human (293 cells), monkey (COS-7 cells), and dog (MDCK cells) were all observed to internalize mAb 3E10 and transport the antibody to the nucleus after only one hour of incubation. The kidney cells remained viable as demonstrated by the exclusion of trypan blue. In contrast, mAb 3E10 did not penetrate human colon cancer cells from LS 174T and HT-29 cell lines. Furthermore, an isotype matched control antibody, PP 102, without DNA binding reactivity did not penetrate any of the kidney cell lines. Antibody penetration and nuclear localization was not observed after only 15 minutes, but it was observed as early as 30 minutes and became maximal at 60 to 90 minutes.

EXAMPLE 5

Mutagenesis of mAb 3E10 Vk

The cloning of mAb 3E10 heavy and light chain cDNA was carried out as previously reported (see, for example, Zack, et al., 1994, supra, and Zack, et al., in *J. Immunol.* 154:1987 (1995)). Site directed mutagenesis of mAb 3E10 VH and Vk was performed by the method of Eckstein et al. (oligonucleotide—directed in vitro mutagenesis system, Amersham Corp., Arlington Heights, Ill.). The VH31 mutant used in these studies has been previously reported (see Zack, et al., 1995, supra). The mutated heavy and light chain cDNAs were ligated into the pSG5 expression vector (Stratagene, La Jolla, Calif.). Individual colonies were selected from transformed competent bacterial cells, and plasmids were prepared using the Wizard DNA purification system (Promega Corp., Madison, Wis.). Mutations were confirmed by dideoxynucleotide sequencing. The oligonucleotides used for mutagenesis of mAb 3E10 Vk are listed below.

Effect of a VH Mutant on Cell Penetration by mAb 3E10

Monoclonal antibody 3E10 heavy and light chain cDNAs were transfected into COS-7 cells and secretion of mAb 3E10 by the transfected COS-7 cells was demonstrated (see, for example, Zack et al., 1995, supra)). Since mAb 3E10 can penetrate COS-7 cells, it was of interest to determine if secreted antibody was reinternalized in cultured cells. Only a small fraction of COS-7 cells produce antibody, thus the concentration of antibody in COS-7 supernatant is in the range of only 30 to 50 ng/ml. This is in marked contrast to concentrations of 10 to 50 μg/ml of purified antibody and 500 ng/ml of hybridoma supernatant required for the demonstration of antibody internalization in previous experiments. As expected, native mAb 3E10 was detected in the cytoplasm in about 1% of COS-7 cells after transfection. However, there was no evidence of translocation to the nucleus, indicating that the pathway by which antibody is secreted bypasses the pathway for nuclear localization. Moreover, the concentration of antibody in the COS-7 cell supernatant was insufficient to detect reentry of antibody into neighboring cells.

A mutant of mAb 3E10 VH has previously been produced involving a change in residue 31 in CDR1 from aspartic acid to asparagine. This mutation increases the ability of the antibody to bind to DNA (see Zack, et al., 1995, supra). Transfection of COS-7 cells with cDNA of the native 3E 10 light chain and cDNA of the VH31 mutant heavy chain resulted in an antibody that was readily observed to penetrate neighboring COS-7 cells and localize in the nucleus. The transfection efficiency was the same for the mutant and native heavy chain cDNAs, and the concentration of the mutant mAb 3E10 in COS-7 cell supernatants was the same as the native antibody.

Effect of mAb 3E10 Vk Mutations on Binding Specificity and Cellular Penetration

In previous studies, mAb 3E10 was used to identify a newly recognized extracellular matrix protein, HP8, in a cDNA expression library (see Zack, et al., 1995, supra). Moreover, DNA and HP8 were shown to share multiple binding determinants on mAb 3E10 VH. In the present studies, mutations in the CDR of mAb 3E10 Vk light chain were observed to eliminate binding to both dsDNA and HP8, dsDNA alone, and HP8 alone (Table I).

| Mutation | CDR | Residue | Oligonucleotide |
| --- | --- | --- | --- |
| SVST deletion | 1 | 27A–D | 5'-TGCAGGGCCAGCAAATCTAGCTATAGT-3' (SEQ ID NO:1) |
| S to D | 1 | 27C | 5'-CAAAAGTGTCGATACATCTAGC-3' (SEQ ID NO:2) |
| Y to F | 1 | 32 | 5'-AGCTATAGTTTCATGCACTGG-3' (SEQ ID NO:3) |
| Q to S | 2 | 53 | 5'-TATGCATCCTCCCTAGAATCT-3' (SEQ ID NO:4) |
| R to N | 3 | 92 | 5'-TCAGCACAGTAATGAGTTTCCGTG-3' (SEQ ID NO:5) |
| F to D | 3 | 94 | 5'-CAGTAGGGAGGATCCGTGGACG-3' (SEQ ID NO:6) |

TABLE I

Effective of mAb 3E10 VH and Vk Mutations on Binding Specificity and Cellular Penetration

| mAb 3E10 | | Mutation | | Antibody Specificity | | Cell entry | |
|---|---|---|---|---|---|---|---|
| | | | | dsDNA | | Cell | |
| H chain | L chain | Location | Change | A | HP8 | COS | 3T3 |
| Native | Native | | | 0.26 | 2.02 | No | No |
| 31 | Native | H CDR1 | D to N | 3.19 | 1.30 | Yes | Yes |
| 31 | 94 | L CDR3 | F to D | 0.50 | 0.20 | No | No |
| 31 | 27 A–D | L CDR1 | Delete | 0.13 | 0.10 | No | No |
| 31 | 92 | L CDR3 | R to N | 0.15 | 1.21 | No | No |
| 31 | 32 | L CDR1 | Y to F | 0.16 | 2.76 | No | No |
| 31 | 27C | L CDR1 | S to D | 3.22 | 0.26 | Yes | Yes |
| 31 | 53 | L CDR2 | Y to S | 2.78 | 0.10 | Yes | Yes |
| No H | No L | | | 0.14 | 0.10 | No | No |

These results are consistent with the previous observations that dsDNA and HP8 share some but not all of binding determinants of mAb 3E10 VH. 3T3 cells have also been shown to express HP8 by Northern hybridization.

In order to further evaluate these differences, the relationship between antibody binding to dsDNA and HP8 and antibody penetration into COS-7 cells and 3T3 cells was studied. COS-7 cells and 3T3 cells were co-transfected with cDNA corresponding to the 3E10 heavy chain 31 mutant and cDNA corresponding to different kappa chain mutants. Cell penetration could not be demonstrated in antibodies containing each of four mutations in mAb 3E10 Vk that eliminated or reduced binding to dsDNA (see Table I). These mutations include residues 27A-D and 32 in CDR1, and residues 92 and 94 in CDR3. Two of the mutations, deletion of 27A-D in CDR1 and alteration of residue 94 in CDR3 eliminated antibody binding to both dsDNA and HP8. The other two mutations, residue 32 in CDR1 and residue 92 in CDR3 removed reactivity with dsDNA but did not affect binding to HP8. If reactivity with HP8 alone was removed, as in the mutation of residue 27C or of residue 53, the mutated antibody retained the ability to penetrate cells as long as the determinants essential for dsDNA binding remained intact. These results suggest that HP8 is not involved in antibody internalization in either of these cell lines. Cellular penetration by mAb 3E10 could be due to the formation of antibody-DNA complexes, or mAb 3E10 may bind a membrane determinant that precisely resembles DNA.

EXAMPLE 6

Molecular Constructs of mAb 3E10 Heavy and Light Chain cDNA mAb 3E10 heavy and light chain cDNA without leader sequences were amplified by PCR using sense primers beginning at FR1 with the addition of the nucleotide sequence ATG. The primers used were:

Heavy chain sense primer:
5'-GCCATGGAGGTGCAGCTGGTGGAGTC-3' (SEQ ID NO:7)

Heavy chain antisense primer:
5'-AATTCTTATTTACCC(A)G(A)GAG T(A)C(G)C(T)GGGGAA(T)(G)GC(G)TCT-3' (SEQ ID NO:8)

Light chain sense primer:
5'-GCCATGGACATTGTGCTGACACAGTC-3' (SEQ ID NO:9)

Light chain antisense primer:
5'-GAATTCTTAACACTCATTCTTGTTGAAGCTCTT-3' (SEQ ID NO:10)

To produce Fab of mAb 3E10, a heavy chain construct was amplified by PCR to contain the heavy chain leader sequence through CH1 and terminating in a stop codon. The primers used were:

Heavy chain sense primer:
5'-ATGGACTCCAGGCTCAATTTAGTTTTC-3' (SEQ ID NO:11)

Heavy chain antisense primer:
5'-TTATTAAATTTTCTTGTCCACTTTGGTG-3' (SEQ ID NO:12)

The conditions used for PCR were: 1 minute denaturation at 95° C., 1 minute annealing at 55° C., and 1.5 minutes extension at 72° C. for 38 cycles with an additional 2 second extension time per cycle.

Localization of mAb 3E10 Devoid of Signal Peptides

To determine if mAb 3E10 is transported to the nucleus as a result of binding cytoplasmic proteins, mAb 3E10 was expressed in COS-7 cells without signal peptide sequences to prevent localization to the endoplasmic reticulum and subsequent secretion from the cell. Histological staining using antibodies to mouse kappa chains demonstrated production of mAb 3E10 and its localization to the cytoplasm. The failure to secrete antibody was shown by the absence of antibody in COS-7 supernatants as measured by ELISA. mAb 3E10 was localized in the cytoplasm, but it was not translocated to the nucleus. Sham transfected COS-7 cells were similarly stained using antibodies to mouse kappa chains as a control.

Penetration of Cells by mAb 3E10 Fab

To investigate the requirement for antibody Fc and multivalent antibody binding in cellular penetration, the cellular penetration of mAb 3E10 Fab was examined. mAb 3E10 heavy chain cDNA, including the leader sequence, VH, and CH1, was amplified by PCR from cDNA of mAb VH31 mutant. The amplified fragment was ligated in pSG5 and co-transfected into COS-7 cells along with mAb 3E10 light chain cDNA. Secretion of antibody Fab by COS-7 cells was confirmed by a capture ELISA with plates coated with goat antibodies to mouse gamma chains (CH1) and detected by goat antibodies to mouse kappa chains. Fab were reinternalized in neighboring cells and found localized in the nucleus as detected by antibodies to mouse gamma chains. Sham transfected COS-7 cells were similarly stained with antibodies to mouse gamma chains as a control. These results eliminate the requirement of Fc and multivalency of antigen binding for cellular penetration by mAb 3E10.

EXAMPLE 7

Expression of Antibodies

Purified pSG5 plasmids containing heavy and light chain gene inserts were expressed in COS-7 mammalian cells. Two micrograms each of plasmid DNA containing a heavy chain cDNA and a light chain cDNA were transfected using DEAE-dextran into $10^5$ COS-7 cells grown in DMEM and 10% fetal calf serum. After three days of culture, the supernatants were harvested and tested by ELISA for the presence of light and heavy chains. The cells were fixed with 70% ethanol for 1 to 2 minutes and washed again multiple times in PBS. The cells were then incubated with alkaline phosphatase conjugated goat anti-mouse antibodies specific for binding IgG2a. The cells were washed in PBS for 3 hours and stained with NBT/BCIP in color development solution containing levamisole.

EXAMPLE 8

Nuclear Delivery of p53 Peptides by Antibody scFv Fragments in Vitro p53 is a nuclear transcription factor that protects cells from replicating damaged DNA by initiating apoptosis in response to alterations in its DNA. Mutations in the DNA binding domain of p53 impair its function permitting unregulated cell proliferation accounting for half of all human malignancies. Restoration of p53 function is an important goal in cancer research. Development of nuclear transport vehicles capable of delivering therapeutics into living cells is a promising approach to restoring p53 function in cancer cells. Experiments were conducted using a single chain antibody fragment of mAb 3E10 to deliver p53 to the nucleus of cancer cells.

Plasmid Constructs mAb 3E10 was produced by fusion of spleen cells from an MRL/lpr/mpj mouse with the FOX-NY hybridoma cell line as described herein. A recombinant scFv fragment containing a myc tag was constructed (as shown in FIG. 1) using VH and Vk cloned from mRNA from hybridoma cells by RT-PCR as previously described (11). In contrast to the scFv reported, the scFv used in these studies was constructed with the Vk 5' of VH, and included the signal peptide of Vk. In addition, myc and $his_6$ tags were added to the C-terminal of VH for purposes of purification and histological localization. The scFv cDNA was constructed by PCR to produce a fusion protein with C-terminal peptides of p53 by ligating the scFv cDNA into the EcoRI and BamHI site of pSG5 (Stratagene, La Jolla, Calif.) and ligating cDNA corresponding to C-terminal peptides of p53 into the BamHI and BglII sites of pSG5. The design of the constructs is shown in FIG. 1A and the plasmid constructs are shown in FIG. 1C. PCR fragments were identified by electrophoresis for 1 hour at 60 milliamps in 0.8% agarose gels containing 0.5 µg/ml ethidium bromide.

The nucleotide primers used to amplify scFv and scFv-p53 cDNA constructs are shown in FIG. 1B. Three p53 C-terminal peptides were produced as fusion proteins with mAb 3E10 scFv, peptide A with 30 amino acids (amino acid residues 364–393); peptide B with 36 amino acids (residues 358–393); peptide C with 50 amino acids (residues 344–393); and a control N-terminal peptide with 48 amino acids (residues 2–49) was produced. In addition, peptide A was produced as a fusion protein with a R95Q mutant of mAb 3E10 VH (pFv-Mut-p53A) that eliminates penetration of mAb 3E10 scFv into living cells (10). The restriction sites of the constructs in pSG5 were changed by PCR to permit ligation of scFv, scFv-p53A, and scFv-p53N into the EcoRI and SacII restriction sites of pPICZαA for subsequent expression in *Pichia pastoris* (EasySelect *Pichia* Expression Kit, Invitrogen Corporation, Carlsbad, Calif.).

Protein Synthesis and Purification pSG5 plasmids containing the cDNA constructs described above were transfected by electroporation into COS-7 cells, and the secreted proteins were purified from culture supernatant by affinity binding to KAPPALOCK™ (Zymed Laboratories, Inc., San Francisco, Calif.). The purified proteins were identified in Western blots of SDS-PAGE gels developed with antibodies to the myc tag in 3E10 scFv. Similarly, pPICZαA containing the constructs of interest were transfected by electroporation into *Pichia pastoris*, and the yeast were grown in 500 ml buffered Glycerol/Methanol Complex Medium (BMGY/BMMY) in 2L baffled shaker flasks. Protein synthesis was induced with 0.5% methanol according to the instructions of the manufacturer (EasySelect *Pichia* Expression Kit, Invitrogen Corporation, Carlsbad, Calif.). Recombinant protein was purified by the $his_6$ tag with NI-NTA-Agarose (Qiagen, Valencia, Calif.), eluted with imidazole, and dialyzed against PBS. Recombinant proteins were electrophoresed in 4–15% gradient SDS-PAGE gels (Biorad laboratories, Hercules, Calif.) and identified by Western blotting to nitrocellulose membranes developed with murine monoclonal antibodies to myc tag (mAb 9E10) and to C-terminal p53 (PAb 421). Western blots were developed with alkaline phosphatase conjugated goat antibodies to mouse IgG. Alkaline phosphatase activity was measured by the chromogenic substrate, nitro blue tetrazolium chloride/5-bromo-4-chloro-3-indolylphosphate p-toluidine salt in color development solution containing levamisole.

Cytotoxic Assays scFv fragments of mAb 3E10 and scFv fusion proteins with peptides of p53 were assayed for cytotoxicity by transfection of plasmids (pSG5) containing cDNA corresponding to these proteins into Green Monkey Kidney cells (COS-7), Chinese hamster cells (CHO) with wild type p53, human colorectal cancer cells (SW480) containing two mutations in p53, His-273/Ser-309, and human osteosarcoma cells (SAOS2). Transfections were done with lipofectamine according to the instructions of the manufacturer (Invitrogen Corporation, Carlsbad, Calif.). Cytotoxicity was also assayed by incubating these cell lines with recombinant proteins produced transiently in COS-7 cells and *Pichia pastoris*. Cell death was measured by the nuclear uptake of propidium iodide (1 µg/ml). Dead cells were observed by fluorescence microscopy with the use of a standard rhodamine filter for red fluorescence. Multiple experiments were done and each experiment contained duplicate determinations. The results were expressed as average percent killed cells determined by counting 300 cells in each well. Differences in the number of killed cells between groups were determined by Student's t test.

Transcriptional Activation of p53

COS-7 cells were cotransfected by electroporation with the plasmids pCD53, pscFv, or pscFv-p53A and the chloramphenicol acetyl transferase (CAT) reporter, pIRG-CAT. $10^6$ cells were cultured in 60 mm diameter Petri dishes for 24 hours in DMEM (Cellgrow, Mediatech, Herndon, Va.) and harvested. The cells were lysed in cell lysis buffer and assayed for CAT by CAT ELISA (Boehringer Mannheim, GmbH, Germany). The results were expressed as the amount of CAT (ng/ml) produced based on a standard curve with known amounts of CAT.

Expression of Recombinant Proteins Containing mAb 3E10 scFv in COS-7 cells cDNA fragments corresponding to p53 A, B and C were PCR amplified and verified on agarose gels. The corresponding peptides were expressed transiently in COS-7 cells, purified from COS-7 supernatant and detected by electrophoresis in 4–15% gradient SDS-PAGE gels identified by mAb 9E 10 that binds the myc tag of scFv and mAb PAb421 that binds the C-terminal of p53.

Each cDNA and polypeptide obtained was of the expected size. The integrity of the fusion proteins was demonstrated by presence of scFv as measured by antibodies (mAb 9E10) to the myc tag of scFv, and the presence of the C-terminus of p53 was demonstrated by binding to PAb421, an anti-p53 antibody. The cDNA sequences were confirmed by automated DNA sequence analysis. The polypeptides were assayed for functional activity by cellular penetration as described below.

scFv-p53 Peptides Penetrate Living Cells

COS-7 cells and SW480 cells were incubated with supernatants of COS-7 cells transfected with the plasmids containing cDNA constructs corresponding to the scFv and scFv-p53 peptides. Staining of the cells showed that mAb 3E10 scFv and scFv-p53A penetrated COS-7 cells and SW480 cells and localized in the nucleus. In contrast, scFvmut-p53A with the mutation R95Q in 3E10 VH did not penetrate living cells. scFv-p53B and C penetrated COS-7 cells and SW480 cells comparable to scFv-p53A. mAb 3E10 scFv and each of the scFv-p53 peptides also penetrated CHO cells and localized in the nucleus.

scFv-p53 Cytotoxicity

Figure 3:
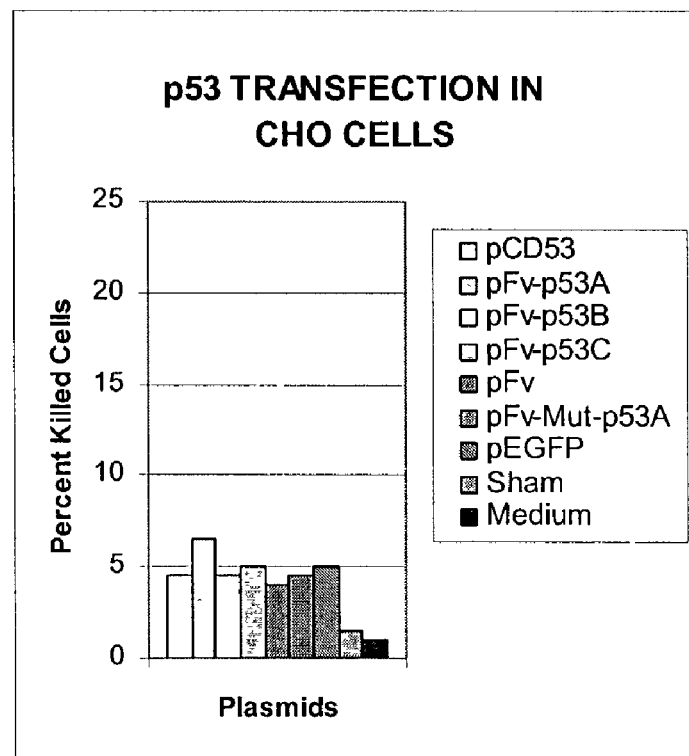
FIG. 3 is a graph showing cytotoxicity of p53 transfection from pscFv-p53A, B, and C transfected into CHO cells.
Figure 4:
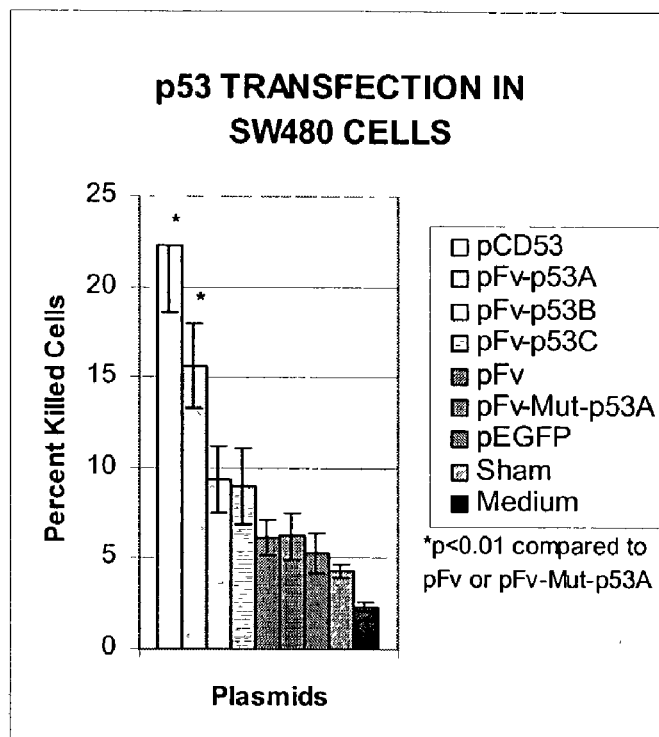
FIG. 4 is a graph showing cytotoxicity of p53 from pscFv-p53A, B, and C transfected into SW480 cancer cells.
Figure 5:
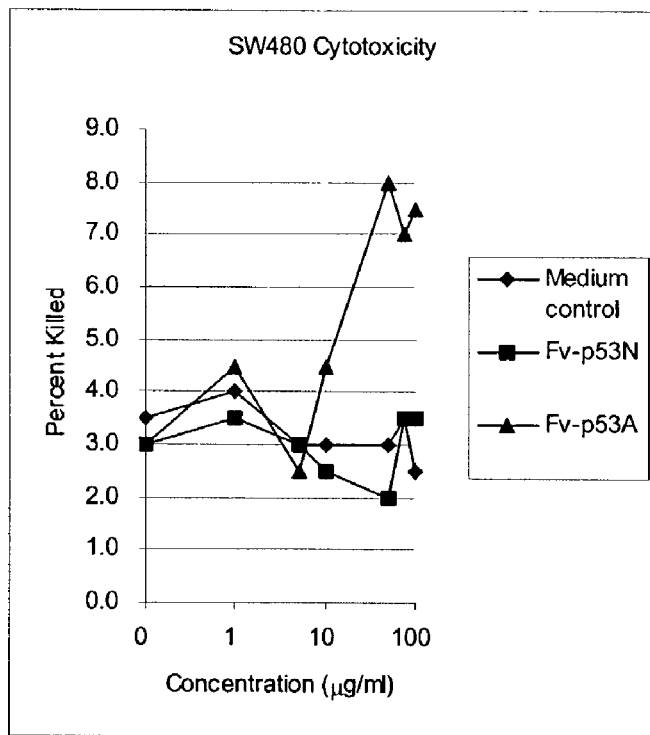
FIG. 5 is a graph showing the dose response of the cytotoxic effect of scFv-p53A.

Plasmids containing cDNA constructs of mAb 3E10 scFv and scFv-p53 fusion proteins were transfected into COS-7, CHO, and SW480 cells (FIG. 1C). Transfection efficiency was determined by transfection with pEGFP and observing the presence of Green Fluorescent Protein by fluorescence microscopy. The transfection efficiency was consistently between 30 and 35% in each cell type and in each of multiple experiments. Transfection of COS-7 and CHO cells with cDNA constructs corresponding to scFv and scFv-p53 peptides did not produce significant cytotoxicity, as shown by the results of these studies presented in FIGS. 2 and 3. In contrast, pscFvp53A produced modest (16%) but significant (p<0.01) killing of SW480 cells compared to pscFv alone, as shown in FIG. 4, where the results represent the mean of 4 separate experiments. Similar experiments in SW480 cells with pCD53 (wild type p53) produced 23% killing, as shown in FIG. 4. However, the maximum killing by p53 would not be expected to exceed the maximum transfection efficiency of 35%. Thus, pCD53 killed 23/30–35% of the cells or approximately 66–77% of transfected cells. On the other hand, scFv-p53A is secreted and re-internalized into all of the cells. Therefore, the total percentage of killing by scFv-p53A is 16% of total cells incorporating the fusion protein. Thus, killing by pscFv-p53A is quite modest in comparison to wild type p53. Fv-Mut-p53A contains the mutation R95Q in 3E10 VH that prevents 3E10 VH from penetrating living cells. pFv-Mut-p53A was not cytotoxic in SW480 cells suggesting that cytotoxicity in response to transfection with pFv-p53A occurred as a result of secreted Fv-p53A protein that was reinternalized.

scFv-p53A protein was then produced in *Pichia pastoris*, purified, and tested for cytotoxicity by adding it directly to cells in tissue culture. scFv alone and scFv-p53N protein (control N-terminal peptide of p53) produced in *Pichia* were used as controls. In a separate experiment, scFv-p53N was shown to penetrate living SW480 cells and localize in the nucleus. Increased killing of COS-7 cells did not occur with any of the scFv-p53 fusion proteins at a concentration of 100 µg/ml. In contrast, incubation of 100 µg/ml of scFv-p53A with SW480 produced modest killing (8% to 10%) compared to 1% to 2% killing by scFv and scFv-p53N alone in three separate experiments (p<0.01). A representative experiment is displayed in FIG. 5. A dose response study showed killing of SW480 cells with as little as 10–25 µg/ml of scFv-p53A; however, no significant enhancement of killing occurred at higher doses. The results of a representative experiment are shown in FIG. 6. In a separate experiment, scFv-P53A did not kill SAOS2 cells devoid of the p53 gene.

Transcriptional Activation by scFv-p53 Peptides scFv-p53A was tested for restoration of transcriptional activation in SW480 cells cotransfected with pscFv-p53A and the pIRG-CA T reporter construct. Whereas pCD53 (wild type p53) induced significant CAT production, no increase in CAT occurred in response to pscFv-p53A. A representative experiment is shown in Table II below. SW480 cells transfected with the reporter pIRG-CA T were also incubated with 100 µg/ml of scFv-p53A protein for 24 hours, and the cells were examined for the production of CAT. scFv-p53A did not increase production of CAT in two separate experiments. These results indicate that transfection with pscFv-p53A or incubation of cells with the scFv-p53A protein did not restore p53 transcriptional activation in SW480 cells.

TABLE II

Effect of Fusion Proteins on p53 Transcriptional Activation

| Plasmid Transfected | CAT (ng/ml) |
|---|---|
| Sham Transfection | 0.00 |
| IRG-CAT Reporter alone | 0.02 |
| pFv | 0.07 |
| IRG-CAT Reporter plus: | |
| pFv-P53A | 0.11 |
| pFv-P53B | 0.10 |
| pFv-P53C | 0.10 |
| PCD53 | 1.00 |

EXAMPLE 9

Cell Type Specific Targeted Intracellular Delivery In Vivo

Because of the ability of mAb 3E10 to transport potential therapeutic proteins into intracellular compartments, the tissue distribution and intracellular localization in vivo after intravenous administration was determined. In this example it is shown that that, in contrast to studies in vitro wherein mAb 3E 10 is shown to penetrate into the nucleus of various cell types, mAb 3E10 is transported selectively into skeletal muscle cells in vivo through binding a nuclear-specific variant of the adult fast IIb myosin heavy chain.

Antibodies and scFv Fragments

Monoclonal antibody 3E10 (mAb 3E10) was established by fusion of spleen cells from an MRL/lpr/mpj mouse with the FOX-NY cell line as previously described herein. cDNA corresponding to functional 3E 10 heavy and light chains were cloned by RT-PCR from mRNA isolated from hybridoma cells, and an scFv fragment was constructed by PCR as previously described (Weisbart et al., 1998). However, the 3E10 scFv used for these studies was redesigned to reverse the order of VH and Vk and place Vk cDNA 5' of VH. The new scFv used the signal peptide of the kappa chain. This modified scFv showed enhanced secretion from COS-7 cells.

mAb 3E 10 heavy and light chain constructs and mutants used in these experiments were previously described (Zack et al., 1996). COS-7 cells were obtained from the American Type Culture Collection (Rockville, Md.) and grown in DMEM with 10% FCS. mAb 3E10 cDNA and various recombinant cDNA constructs were ligated into the cloning site of pSG5 (Stratagene, La Jolla, Calif.). Plasmids were transfected into COS-7 cells by electroporation for transient production of recombinant proteins. Supernatants of COS-7 cells were used as a source of mAb 3E 10 to identify antigens in tissue lysates reactive with the antibody by Western blotting.

scFv cDNA was ligated into the cloning site of pPICZαA, transfected into Pichia pastoris by electroporation, and selected with Zeocin according to the manufacturer's instructions (EasySelect Pichia Expression Kit, Invitrogen Corporation, Carlsbad, Calif.). Clones with the highest levels of secreted scFv were identified by antibody screening (Wung and Gascoigne, 2002). Pichia pastoris was grown in 500 ml buffered Glycerol/Methanol Complex Medium (BMGY/BMMY) in 2L baffled shake flasks, and protein expression was induced with 0.5% methanol. 3E10 scFv containing a 3'-terminal his$_6$ tag was purified with NI-NTA-Agarose (Qiagen, Valencia, Calif.) and dialyzed with PBS.

A murine monoclonal antibody was obtained that was specific for binding skeletal muscle myosin (Sigma-Aldrich Fine Chemicals, St. Louis, Mo.).

Cellular Penetration of 3E10 scFv In Vivo

3E10 scFv-his$_6$ (50 micrograms in 50 microliters saline vehicle) was injected into the tail veins of normal FVB mice. After 4 hours, the mice were anesthetized by inhalation and the circulation was perfused with saline through a cannula inserted into the heart. Samples of tissues were snap frozen in chilled 2-methylbutane at −70° C. in liquid nitrogen. Tissues were cut in 10 μm sections by cryostat and fixed in 75% alcohol for 20 min. Sectioned tissues were incubated with goat anti-his$_6$ antibody conjugated with horseradish peroxidase 1:500 (Invitrogen Corporation, Carlsbad, Calif.) at 37° C. for 1 hr, washed and developed with the Metal Enhanced DAB Substrate Kit (Pierce Chemical Company, Rockford, Ill.), and cellular localization of the dark brown deposit was identified by light microscopy.

Mice Null for Myosin Heavy Chains

Mice null for myosin IIb and IId were previously described (Allen and Leinwand, 2001). Lysates were prepared from skeletal muscle tissue from wild type (wt) mice and mice null for myosin IIb and IId. The lysates were analyzed by Western blotting for binding antibody.

Tissue Lysates

Tissues were homogenized in a Dounce Homogenizer, and cytoplasmic and nuclear lysates were prepared with NE-PER Nuclear and Cytoplasmic Extraction Reagents (Pierce Chemical Company) according to the manufacturer's protocol.

Electrophoresis and Western Blotting

Electrophoresis samples were diluted 1:2 in sample buffer containing 2% SDS, boiled, and applied to 4%–15% tris-HCl polyacrylamide gradient gels (4–15% Ready Gel Tris-HCl, Bio Rad Laboratories, Hercules, Calif.). The gels were electrophoresed at 140 volts for 90 min in tris/glycine/SDS buffer (Protein Electrophoresis Buffer, Bio Rad Laboratories, Hercules, Calif.). The gels were stained with either GELCODE BLUE® Stain Reagent (Pierce Chemical Company), or the proteins were transblotted to nitrocellulose in Blotting Transfer Buffer, 25 mM Tris, 192 mM Glycine, pH 8.3 (Bio Rad Laboratories, Hercules, Calif.). As an alternative, concentrated HCl was added to the blotting transfer buffer to adjust the final pH of the buffer to 8.1. Western blots were developed with 3E 10 hybridoma supernatant or purified mAb 3E10. mAb 3E10 was then measured by alkaline phosphatase-conjugated goat antibodies to mouse gamma chains. Alkaline phosphatase activity was measured by the chromogenic substrate, nitro blue tetrazolium chloride/5-bromo-4-chloro-3-indolylphosphate p-toluidine salt in color development solution containing levamisole.

Antibody Affinity Chromatography

Separate columns of Immunopure Immobilized rprotein-A (Pierce Chemical Company) were saturated with murine monoclonal antibodies mAb PP 102 and mAb 3E 10 and washed with 0.05 M sodium borate buffer, pH 8.0, then 0.02 M tris buffered saline containing 0.5 M NaCl, pH 7.4. Nuclear lysates prepared from rat skeletal muscle were passed through the PP102 column, and the column was washed with 0.05 M sodium borate, pH 8.0 containing 0.1% SDS. Samples of the Sepharose beads were diluted 1:2 in sample buffer containing 2% SDS, and analyzed by SDS-PAGE and Western blotting. The effluent from the PP102 column was then passed through the 3E10 column. The column was then washed and samples of beads were processed and analyzed similarly.

Antibody Specificity for Skeletal Muscle mAb 3E10 was assayed by Western blotting for binding proteins in cytoplasmic and nuclear lysates prepared from multiple tissues to identify target antigens responsible for its transport into living cells in vivo. In preliminary experiments different conditions were used to transblot proteins in tissue lysates from acrylamide gels to nitrocellulose. mAb 3E10 did not bind proteins transferred to nitrocellulose in standard transblot buffer, pH 8.3. However, if the transblot buffer was adjusted to pH 8.1, a 200 kDa protein from skeletal muscle nuclear lysates was transferred that showed prominent binding by mAb 3E10 at about 132 kDa. In contrast, in this test the antibody did not bind a similar protein in nuclear lysates from heart muscle or other tissues, including kidney, lung, liver, spleen, ovary, and brain, and peripheral blood cells. The 200 kDa muscle protein reactive with mAb 3E10 was not present in a control blot developed with second antibody alone. In addition, mAb 3E10 did not bind proteins in cytoplasmic lysates from any of these tissues. In similar tests, it was shown that three other murine monoclonal anti-dsDNA antibodies of the same isotype (5C5, 5C6 and 4H2) did not bind to the 200 kDa protein in skeletal muscle nuclear lysates, indicating binding specificity of mAb 3E10 to the skeletal muscle protein.

Binding Specificity of Recombinant Antibody and scFv Fragments

Single chain Fv fragments (scFv) of mAb 3E10 were produced, and in preliminary studies, the scFv fragments were shown to bind dsDNA and penetrate living cells in vitro comparable to mAb 3E10 (Weisbart et al., 1998, supra). Recombinant 3E10 and scFv were tested for binding the 200 kDa protein in nuclear lysates from skeletal muscle. Recombinant antibody was expressed transiently in COS-7 cells transfected with pSG5 plasmids containing antibody cDNA constructs, and the supernatants were used to test for binding of antibody to the 200 kDa protein by Western blotting. The heavy chain of mAb 3E10 was previously shown to be associated with two separate light chains, only one of which binds dsDNA and penetrates living cells in combination with the heavy chain (Zack et al., 1995). The Western blots in this study showed that mAb 3E10 heavy chain in combination with the anti-dsDNA kIII light chain bound the 200 kDa protein but not in combination with the kVser light chain. A single mutation in CDR3 of the heavy chain, R95Q, was previously reported to eliminate binding of mAb 3E10 to dsDNA and prevent its transport into living cells in vitro. The R95Q mutation also prevented mAb 3E 10 from binding the 200 kDa protein from skeletal muscle nuclear lysate. The scFv containing 3E10 VH and VkIII also bound the 200 kDa protein in a Western blot. These results indicate the use of shared antibody determinants for binding dsDNA and the 200 kDa protein, and demonstrate that scFv fragments bind the 200 kDa protein similar to whole antibody.

Localization of Antibody to Skeletal Muscle Nuclei In Vivo

Vehicle or 3E10 scFv fragments (50 micrograms in 50 microliters of saline) were infused into the tail veins of FVB mice to study distribution of the antibody in vivo. Four hours after injection, the animals were anesthetized by inhalation and the circulation was perfused with saline through a cannula inserted into the heart. Samples of tissues were snap frozen and kept at −80° C. Multiple tissues were sectioned by cryostat and stained with peroxidase-conjugated antibodies directed to the $his_6$ tag of scFv fragments. Histological analysis of stained samples showed that scFv fragments were found predominantly in the nuclei of about 20% of skeletal muscle cells. scFv fragments were also found infrequently in the nuclei of renal tubular cells. The relatively small amount of antigen in kidney may explain the failure to identify reactivity of mAb 3E10 in Western blots of lysates from kidney. scFv fragments were not found in any other tissues, including brain, lung, intestine, spleen, liver, pancreas, ovary, and skin. The heart muscle was inadequately perfused with saline, so localization of antibody in heart muscle could not be evaluated adequately. Sections from vehicle injected control mouse tissues showed no antibody label. These results demonstrate the relative specificity of mAb 3E10 scFv fragments for penetrating skeletal muscle cells in vivo.

Antibody Affinity Purification

Nuclear lysates of rat skeletal muscle were passed through a column containing immobilized recombinant protein-A saturated with an IgG 2a isotype control antibody, mAb PP102, with unknown binding specificity. The effluent was then passed through a protein-A-Sepharose column saturated with mAb 3E10. The affinity columns were washed with 0.05M borate buffer, pH 8.0 containing 0.1% SDS, and a sample of beads from each was boiled in 2% SDS, electrophoresed in a 4%–15% gradient acrylamide gel, and stained with GELCODE BLUE® stain (Pierce Chemical Company). A separate sample was transblotted to nitrocellulose and developed with mAb 3E10. The results of these studies showed the proteins contained in skeletal muscle nuclear lysate were stained with GELCODE BLUE®. The absence of non-specific binding of nuclear proteins to the column containing the control mAb PP102 antibody was also demonstrated. The antibody heavy chain (50 kDa) and light chain (25 kDa) were identified as expected, since the antibody was not cross-linked to the protein-A column. In contrast, several proteins in addition to the 3E10 heavy chain (50 kDa) and two light chains (25 kDa and 28 kDa) were identified by the staining. A 200 kDa protein visualized by staining was identified as corresponding to the 200 kDa protein visualized by Western blot (lane 4) that demonstrates binding by mAb 3E10. The 200 kDa protein was excised from the gel and identified by electrospray mass spectrometry (Nano-LC/MS/MS). The analysis was done in the Howard Hughes Institute, Columbia University, N.Y.

Nano-LC/MS/MS

Analysis of the 200 kDa protein from rat skeletal muscle by Nano-LC/MS/MS resulted in 28 peptides that showed complete identity with human myosin IIb (SEQ ID NO:13. (FIG. 6). There was no other identifiable protein. To confirm the identity of myosin as the protein reactive with mAb 3E 10, affinity purification of the 200 kDa protein from skeletal muscle nuclear lysate was performed using mAb 3E10 bound to protein-A-Sepharose. The purified protein was examined for binding a monoclonal anti-myosin antibody in a Western blot. The anti-myosin antibody bound the 200 kDa protein affinity purified with mAb 3E10.

Antibody Binding to Myosin Heavy Chains from Mice Null for Myosin Heavy Chains Iib and IId To further confirm that mAb 3E10 binds myosin IIb, the antibody was used to develop Western blots of skeletal muscle lysates from mice null for myosin IIb and IId. A control anti-myosin antibody confirmed the presence of myosin IIb in mice null for IId and myosin IId in mice null for myosin IIb. In contrast, mAb 3E10 bound a 200 kDa skeletal muscle protein from wild type mice and mice null for myosin IId, but not from mice null for myosin IIb. This result confirmed that mAb 3E10 binds mouse myosin IIb.

In preliminary studies, myosin was transblotted to nitrocellulose in standard transblot buffer, but the 200 kDa protein reactive with mAb 3E10 required a less alkaline buffer. This result suggested that mAb 3E10 was binding a specific isoform of myosin IIb. This result was evaluated further by performing Western blots and comparing results obtained with standard transblot buffer, pH 8.3, and standard buffer adjusted to pH 8.1. In these studies, myosin contained in muscle lysates from wild type mice and mice null for myosin heavy chain IIb and IId was transferred to nitrocellulose in standard buffer as shown by development with a known anti-myosin antibody. However mAb 3E10 did not bind myosin IIb under standard transblot conditions. In contrast, the myosin IIb reactive with mAb 3E10 was transferred successfully to nitrocellulose in transblot buffer adjusted to pH 8.1. These results confirm that mAb 3E10 binds myosin IIb. However, mAb 3E10 binds only myosin IIb transblotted at pH 8.1, indicating that mAb 3E10 likely binds a specific isoform variant of myosin IIb.

Myosin IIb Isoform in Muscle Nuclei

The isoform of myosin IIb reactive with mAb 3E10 was identified primarily in nuclear, but not cytoplasmic lysates, of skeletal muscle cells. To localize this myosin isoform in tissue, 3E10 scFv was examined for binding fixed skeletal muscle. In these studies, 3E10 scFv bound to the nucleus only, but was distributed in an unusual pattern. Examination of cross-sections of skeletal muscle showed irregular nuclear deposition of antibody compared to the characteristic "ring" pattern of nuclear binding to DNA observed in other cells. The pattern of nuclear staining usually observed was shown in cross sections of heart muscle for comparison. This finding is consistent with 3E10 binding an isoform of myosin IIb localized in the nucleus of skeletal muscle cells. There appears to be preferential binding of antibody to nuclear myosin IIb in skeletal muscle cells in contrast to binding to native DNA in the nuclei of cells from other tissues. This result indicates that mAb 3E10 has greater binding affinity to myosin IIb than to dsDNA and suggests that the binding of mAb 3E10 to dsDNA may be the result of cross-reactivity with an isoform of myosin IIb.

While the invention has been described in detail with reference to certain preferred embodiments thereof, it will be understood that modifications and variations are within the spirit and scope of that which is described and claimed.

That which is claimed is:

1. A method for transporting a biologically active molecule into the nucleus of a target cell in vitro, comprising:
    a) combining said biologically active molecule in vitro with monoclonal antibody (mAb) 3E10 as produced by a hybridoma having ATCC accession number PTA 2439 or an scFv fragment thereof, to form an antibody-biologically active molecule conjugate or fusion protein, and
    b) contacting the target cell in vitro under suitable conditions with the antibody-biologically active molecule conjugate of a), thereby transporting the biologically active molecule into the nucleus of the target cell.

2. The method of claim 1 wherein said biologically active molecule is a nuclear transcription factor, an enzyme, an enzyme inhibitor, genetic material, an inorganic or organic molecule, a pharmaceutical agent, a drug, or a polypeptide.

3. The method of claim 2, wherein the biologically active molecule is a polypeptide.

4. The method of claim 1, wherein the antibody is the scFv fragment.

5. The method of claim 4, wherein the biologically active molecule is a polypeptide.

6. The method of claim 1, wherein the contacting comprises incubating the cells in the presence of the conjugate or a fusion protein.

7. The method of claim 1, wherein the scFv fragment comprises the variable region of the heavy chain (VH) and variable region of the kappa light chain (Vκ) of mAb 3E10.

8. The method of claim 7, wherein the scFv fragment further comprises the signal peptide of the Vκ.

9. The method of claim 1, wherein the biologically active molecule is a p53 polypeptide.

10. The method of claim 9, wherein the target cell is a cancer cell.

* * * * *

SEQUENCE LISTING

<160> NUMBER OF SEQ ID NOS: 29

<210> SEQ ID NO 1
<211> LENGTH: 27
<212> TYPE: DNA
<213> ORGANISM: Artificial Sequence
<220> FEATURE:
<223> OTHER INFORMATION: oligonucleotide used for mutagenesis

<400> SEQUENCE: 1
tgcagggcca gcaaatctag ctatagt                27

<210> SEQ ID NO 2
<211> LENGTH: 22
<212> TYPE: DNA
<213> ORGANISM: Artificial Sequence
<220> FEATURE:
<223> OTHER INFORMATION: oligonucleotide used for mutagenesis

<400> SEQUENCE: 2
caaaagtgtc gatacatcta gc                22

<210> SEQ ID NO 3
<211> LENGTH: 21
<212> TYPE: DNA
<213> ORGANISM: Artificial Sequence
<220> FEATURE:
<223> OTHER INFORMATION: oligonucleotide used for mutagenesis

<400> SEQUENCE: 3
agctatagtt tcatgcactg g                21

<210> SEQ ID NO 4
<211> LENGTH: 21
<212> TYPE: DNA
<213> ORGANISM: Artificial Sequence
<220> FEATURE:
<223> OTHER INFORMATION: oligonucleotide used for mutagenesis

<400> SEQUENCE: 4
tatgcatcct ccctagaatc t                21

<210> SEQ ID NO 5
<211> LENGTH: 24
<212> TYPE: DNA
<213> ORGANISM: Artificial Sequence
<220> FEATURE:
<223> OTHER INFORMATION: oligonucleotide used for mutagenesis

<400> SEQUENCE: 5
tcagcacagt aatgagtttc cgtg                24

<210> SEQ ID NO 6
<211> LENGTH: 22
<212> TYPE: DNA
<213> ORGANISM: Artificial Sequence
<220> FEATURE:
<223> OTHER INFORMATION: oligonucleotide used for mutagenesis

<400> SEQUENCE: 6
cagtagggag gatccgtgga cg                22

<210> SEQ ID NO 7
<211> LENGTH: 26
<212> TYPE: DNA
<213> ORGANISM: Artificial Sequence
<220> FEATURE:
<223> OTHER INFORMATION: heavy chain sense primer

<400> SEQUENCE: 7
gccatggagg tgcagctggt ggagtc        26

<210> SEQ ID NO 8
<211> LENGTH: 41
<212> TYPE: DNA
<213> ORGANISM: Artificial Sequence
<220> FEATURE:
<223> OTHER INFORMATION: heavy chain antisense primer

<400> SEQUENCE: 8
aattcttatt tacccagaga gtacgctggg gaatggcgtc t        41

<210> SEQ ID NO 9
<211> LENGTH: 26
<212> TYPE: DNA
<213> ORGANISM: Artificial Sequence
<220> FEATURE:
<223> OTHER INFORMATION: light chain sense primer

<400> SEQUENCE: 9
gccatggaca ttgtgctgac acagtc        26

<210> SEQ ID NO 10
<211> LENGTH: 33
<212> TYPE: DNA
<213> ORGANISM: Artificial Sequence
<220> FEATURE:
<223> OTHER INFORMATION: light chain antisense primer

<400> SEQUENCE: 10
gaattcttaa cactcattct tgttgaagct ctt        33

<210> SEQ ID NO 11
<211> LENGTH: 27
<212> TYPE: DNA
<213> ORGANISM: Artificial Sequence
<220> FEATURE:
<223> OTHER INFORMATION: heavy chain sense primer

<400> SEQUENCE: 11
atggactcca ggctcaattt agttttc        27

<210> SEQ ID NO 12
<211> LENGTH: 28
<212> TYPE: DNA
<213> ORGANISM: Artificial Sequence
<220> FEATURE:
<223> OTHER INFORMATION: heavy chain antisense primer

<400> SEQUENCE: 12
ttattaaatt ttcttgtcca ctttggtg        28

<210> SEQ ID NO 13
<211> LENGTH: 1725
<212> TYPE: PRT
<213> ORGANISM: Homo sapiens

<400> SEQUENCE: 13

```
Met Gln Gly Thr Leu Glu Asp Gln Ile Ile Ser Ala Asn Pro Leu Leu
1               5                   10                  15

Glu Ala Phe Gly Asn Ala Lys Thr Val Arg Asn Asp Asn Ser Ser Arg
            20                  25                  30

Phe Gly Lys Phe Ile Arg Ile His Phe Gly Ala Thr Gly Lys Leu Ala
        35                  40                  45

Ser Ala Asp Ile Glu Thr Tyr Leu Leu Glu Lys Ser Arg Val Thr Phe
    50                  55                  60

Gln Leu Lys Ala Glu Arg Ser Tyr His Ile Phe Tyr Gln Ile Leu Ser
65                  70                  75                  80

Asn Lys Lys Pro Glu Leu Ile Glu Met Leu Leu Ile Thr Thr Asn Pro
                85                  90                  95

Tyr Asp Phe Ala Phe Val Ser Gln Gly Glu Ile Thr Val Pro Ser Ile
            100                 105                 110

Asp Asp Gln Glu Glu Leu Met Ala Thr Asp Ser Ala Val Asp Ile Leu
            115                 120                 125

Gly Phe Thr Ala Asp Glu Lys Val Ala Ile Tyr Lys Leu Thr Gly Ala
        130                 135                 140

Val Met His Tyr Gly Asn Met Lys Phe Lys Gln Lys Gln Arg Glu Glu
145                 150                 155                 160

Gln Ala Glu Pro Asp Gly Thr Glu Val Ala Asp Lys Ala Ala Tyr Leu
                165                 170                 175

Thr Ser Leu Asn Ser Ala Asp Leu Leu Lys Ser Leu Cys Tyr Pro Arg
            180                 185                 190

Val Lys Val Gly Asn Glu Phe Val Thr Lys Gly Gln Thr Val Gln Gln
            195                 200                 205

Val Tyr Asn Ala Val Gly Ala Leu Ala Lys Ala Ile Tyr Glu Lys Met
        210                 215                 220

Phe Leu Trp Met Val Thr Arg Ile Asn Gln Gln Leu Asp Thr Lys Gln
225                 230                 235                 240

Pro Arg Gln Tyr Phe Ile Gly Val Leu Asp Ile Ala Gly Phe Glu Ile
                245                 250                 255

Phe Asp Phe Asn Ser Leu Glu Gln Leu Cys Ile Asn Phe Thr Asn Glu
            260                 265                 270

Lys Leu Gln Gln Phe Phe Asn His His Met Phe Val Leu Glu Gln Glu
        275                 280                 285

Glu Tyr Lys Lys Glu Gly Ile Glu Trp Glu Phe Ile Asp Phe Gly Met
    290                 295                 300

Asp Leu Ala Ala Cys Ile Glu Leu Ile Glu Lys Pro Met Gly Ile Phe
305                 310                 315                 320

Ser Ile Leu Glu Glu Glu Cys Met Phe Pro Lys Ala Thr Asp Thr Ser
                325                 330                 335

Phe Lys Asn Lys Leu Tyr Glu Gln His Leu Gly Lys Ser Asn Asn Phe
            340                 345                 350

Gln Lys Pro Lys Pro Ala Lys Gly Lys Pro Glu Ala His Phe Ser Leu
        355                 360                 365

Val His Tyr Ala Gly Thr Val Asp Tyr Asn Ile Ala Gly Trp Leu Asp
    370                 375                 380

Lys Asn Lys Asp Pro Leu Asn Glu Thr Val Val Gly Leu Tyr Gln Lys
385                 390                 395                 400

Ser Ala Met Lys Thr Leu Ala Phe Leu Phe Ser Gly Ala Gln Thr Ala
                405                 410                 415
```

-continued

```
Glu Ala Glu Gly Gly Gly Lys Lys Gly Gly Lys Lys Lys Gly Ser
            420                 425             430

Ser Phe Gln Thr Val Ser Ala Leu Phe Arg Glu Asn Leu Asn Lys Leu
            435                 440                 445

Met Thr Asn Leu Arg Ser Thr His Pro His Phe Val Arg Cys Ile Ile
    450                 455                 460

Pro Asn Glu Thr Lys Thr Pro Gly Ala Met Glu His Glu Leu Val Leu
465                 470                 475                 480

His Gln Leu Arg Cys Asn Gly Val Leu Glu Gly Ile Arg Ile Cys Arg
                485                 490                 495

Lys Gly Phe Pro Ser Arg Ile Leu Tyr Ala Asp Phe Lys Gln Arg Tyr
            500                 505                 510

Lys Val Leu Asn Ala Ser Ala Ile Pro Glu Gly Gln Phe Ile Asp Ser
            515                 520                 525

Lys Lys Ala Ser Glu Lys Leu Leu Gly Ser Ile Glu Ile Asp His Thr
530                 535                 540

Gln Tyr Lys Phe Gly His Thr Lys Val Phe Phe Lys Ala Gly Leu Leu
545                 550                 555                 560

Gly Thr Leu Glu Glu Met Arg Asp Glu Lys Leu Ala Gln Leu Ile Thr
            565                 570                 575

Arg Thr Gln Ala Ile Cys Arg Gly Phe Leu Met Arg Val Glu Phe Arg
            580                 585                 590

Lys Met Met Glu Arg Arg Glu Ser Ile Phe Cys Ile Gln Tyr Asn Ile
            595                 600                 605

Arg Ala Phe Met Asn Val Lys His Trp Pro Trp Met Lys Leu Tyr Phe
            610                 615                 620

Lys Ile Lys Pro Leu Leu Lys Ser Ala Glu Thr Glu Lys Glu Met Ala
625                 630                 635                 640

Asn Met Lys Glu Glu Phe Glu Lys Thr Lys Glu Glu Leu Ala Lys Thr
                645                 650                 655

Glu Ala Lys Arg Lys Glu Leu Glu Glu Lys Met Val Thr Leu Met Gln
            660                 665                 670

Glu Lys Asn Asp Leu Gln Leu Gln Val Gln Ala Glu Ala Asp Ala Leu
            675                 680                 685

Ala Asp Ala Glu Glu Arg Cys Asp Gln Leu Ile Lys Thr Lys Ile Gln
690                 695                 700

Leu Glu Ala Lys Ile Lys Glu Val Thr Glu Arg Ala Glu Asp Glu Glu
705                 710                 715                 720

Glu Ile Asn Ala Glu Leu Thr Ala Lys Lys Arg Lys Leu Glu Asp Glu
                725                 730                 735

Cys Ser Glu Leu Lys Lys Asp Ile Asp Asp Leu Glu Leu Thr Leu Ala
            740                 745                 750

Lys Val Glu Lys Glu Lys His Ala Thr Glu Asn Lys Val Lys Asn Leu
            755                 760                 765

Thr Glu Glu Met Ala Gly Leu Asp Glu Thr Ile Ala Lys Leu Thr Lys
770                 775                 780

Glu Lys Lys Ala Leu Gln Glu Ala His Gln Gln Thr Leu Asp Asp Leu
785                 790                 795                 800

Gln Met Glu Glu Asp Lys Val Asn Thr Leu Thr Lys Ala Lys Thr Lys
                805                 810                 815

Leu Glu Gln Gln Val Asp Asp Leu Glu Gly Ser Leu Glu Gln Glu Lys
            820                 825                 830
```

```
Lys Leu Cys Met Asp Leu Glu Arg Ala Lys Arg Lys Leu Glu Gly Asp
            835                 840                 845
Leu Lys Leu Ala Gln Glu Ser Thr Met Asp Thr Glu Asn Asp Lys Gln
850                 855                 860
Gln Leu Asn Glu Lys Leu Lys Lys Glu Phe Glu Met Ser Asn Leu
865                 870                 875                 880
Gln Gly Lys Ile Glu Asp Glu Gln Ala Leu Ala Ile Gln Leu Gln Lys
            885                 890                 895
Lys Ile Lys Glu Leu Gln Ala Arg Ile Glu Glu Leu Glu Glu Glu Ile
                900                 905                 910
Glu Ala Glu Arg Ala Ser Arg Ala Lys Ala Glu Lys Gln Arg Ser Asp
            915                 920                 925
Leu Ser Arg Glu Leu Glu Glu Ile Ser Glu Arg Leu Glu Glu Ala Gly
            930                 935                 940
Gly Ala Thr Ser Ala Gln Ile Glu Met Asn Lys Lys Arg Glu Ala Glu
945                 950                 955                 960
Phe Gln Lys Met Arg Arg Asp Leu Glu Glu Ser Thr Leu Gln His Glu
                965                 970                 975
Ala Thr Ala Ala Ala Leu Arg Lys Lys His Ala Asp Ser Val Ala Glu
            980                 985                 990
Leu Gly Glu Gln Ile Asp Ser Leu Gln Arg Val Lys Gln Lys Leu Glu
            995                 1000                1005
Lys Glu Lys Ser Glu Leu Lys Met Glu Ile Asn Asp Leu Ala Ser
1010                1015                1020
Asn Met Glu Thr Val Ser Lys Ala Lys Ala Asn Phe Glu Lys Met
1025                1030                1035
Cys Arg Thr Leu Glu Asp Gln Leu Ser Glu Ile Lys Thr Lys Glu
1040                1045                1050
Glu Glu Gln Gln Arg Leu Ile Asn Glu Leu Ser Ala Gln Lys Ala
1055                1060                1065
Arg Leu His Thr Glu Ser Gly Glu Phe Ser Arg Gln Leu Asp Glu
1070                1075                1080
Lys Asp Ala Met Val Ser Gln Leu Ser Arg Gly Lys Gln Ala Phe
1085                1090                1095
Thr Gln Gln Ile Glu Glu Leu Lys Arg Gln Leu Glu Glu Glu Thr
1100                1105                1110
Lys Ala Lys Ser Thr Leu Ala His Ala Leu Gln Ser Ala Arg His
1115                1120                1125
Asp Cys Asp Leu Leu Arg Glu Gln Tyr Glu Glu Glu Gln Glu Ala
1130                1135                1140
Lys Ala Glu Leu Gln Arg Gly Met Ser Lys Ala Asn Ser Glu Val
1145                1150                1155
Ala Gln Trp Arg Thr Lys Tyr Glu Thr Asp Ala Ile Gln Arg Thr
1160                1165                1170
Glu Glu Leu Glu Glu Ala Lys Lys Lys Leu Ala Gln Arg Leu Gln
1175                1180                1185
Asp Ala Glu Glu His Val Glu Ala Val Asn Ser Lys Cys Ala Ser
1190                1195                1200
Leu Glu Lys Thr Lys Gln Arg Leu Gln Asn Glu Val Glu Asp Leu
1205                1210                1215
Met Ile Asp Val Glu Arg Ser Asn Ala Ala Cys Ile Ala Leu Asp
1220                1225                1230
```

-continued

| | | | | | | | | | | | |
|---|---|---|---|---|---|---|---|---|---|---|---|
| Lys | Lys | Gln | Arg | Asn | Phe | Asp | Lys | Val | Leu | Ala | Glu | Trp | Lys | Gln |
| 1235 | | | | 1240 | | | | | 1245 | | |

Lys Lys Gln Arg Asn Phe Asp Lys Val Leu Ala Glu Trp Lys Gln
1235                1240                   1245

Lys Tyr Glu Glu Thr Gln Ala Glu Leu Glu Ala Ser Gln Lys Glu
1250                1255                   1260

Ser Arg Ser Leu Ser Thr Glu Leu Phe Lys Val Lys Asn Ala Tyr
1265                1270                   1275

Glu Glu Ser Leu Asp His Leu Glu Thr Leu Lys Arg Glu Asn Lys
1280                1285                   1290

Asn Leu Gln Gln Glu Ile Ser Asp Leu Thr Glu Gln Ile Ala Glu
1295                1300                   1305

Gly Gly Lys His Ile His Glu Leu Glu Lys Val Lys Lys Gln Leu
1310                1315                   1320

Asp His Glu Lys Ser Glu Leu Gln Thr Ser Leu Glu Glu Ala Glu
1325                1330                   1335

Ala Ser Leu Glu His Glu Glu Gly Lys Ile Leu Arg Ile Gln Leu
1340                1345                   1350

Glu Leu Asn Gln Val Lys Ser Glu Ile Asp Arg Lys Ile Ala Glu
1355                1360                   1365

Lys Asp Glu Glu Leu Asp Gln Leu Lys Arg Asn His Leu Arg Val
1370                1375                   1380

Val Glu Ser Met Gln Ser Thr Leu Asp Ala Glu Ile Arg Ser Arg
1385                1390                   1395

Asn Asp Ala Leu Arg Ile Lys Lys Lys Met Glu Gly Asp Leu Asn
1400                1405                   1410

Glu Met Glu Ile Gln Leu Asn His Ala Asn Arg Gln Ala Ala Glu
1415                1420                   1425

Ala Leu Arg Asn Leu Arg Asn Thr Gln Gly Ile Leu Lys Asp Thr
1430                1435                   1440

Gln Leu His Leu Asp Asp Ala Ile Arg Gly Gln Asp Asp Leu Lys
1445                1450                   1455

Glu Gln Leu Ala Met Val Glu Arg Arg Ala Asn Leu Met Gln Ala
1460                1465                   1470

Glu Val Glu Glu Leu Arg Ala Ser Leu Glu Arg Thr Glu Arg Gly
1475                1480                   1485

Arg Lys Met Ala Glu Gln Glu Leu Leu Asp Ala Ser Glu Arg Val
1490                1495                   1500

Gln Leu Leu His Thr Gln Asn Thr Ser Leu Ile Asn Thr Lys Lys
1505                1510                   1515

Lys Leu Glu Thr Asp Ile Ser Gln Ile Gln Gly Glu Met Glu Asp
1520                1525                   1530

Ile Val Gln Glu Ala Arg Asn Ala Glu Glu Lys Ala Lys Lys Ala
1535                1540                   1545

Ile Thr Asp Ala Ala Met Met Ala Glu Glu Leu Lys Lys Glu Gln
1550                1555                   1560

Asp Thr Ser Ala His Leu Glu Arg Met Lys Lys Asn Met Glu Gln
1565                1570                   1575

Thr Val Lys Asp Leu Gln Leu Arg Leu Asp Glu Ala Glu Gln Leu
1580                1585                   1590

Ala Leu Lys Gly Gly Lys Lys Gln Ile Gln Lys Leu Glu Ala Arg
1595                1600                   1605

Val Arg Glu Leu Glu Ser Glu Val Glu Ser Glu Gln Lys His Asn
1610                1615                   1620

```
Val Glu Ala Val Lys Gly Leu Arg Lys His Glu Arg Arg Val Lys
    1625                1630                1635

Glu Leu Thr Tyr Gln Thr Glu Glu Asp Arg Lys Asn Ile Leu Arg
    1640                1645                1650

Leu Gln Asp Leu Val Asp Lys Leu Gln Thr Lys Val Lys Ala Tyr
    1655                1660                1665

Lys Arg Gln Ala Glu Glu Ala Glu Glu Gln Ser Asn Val Asn Leu
    1670                1675                1680

Ala Lys Phe Arg Lys Leu Gln His Glu Leu Glu Ala Lys Glu
    1685                1690                1695

Arg Ala Asp Ile Ala Glu Ser Gln Val Asn Lys Leu Arg Val Lys
    1700                1705                1710

Ser Arg Glu Val His Thr Lys Val Ile Ser Glu Glu
    1715                1720                1725

<210> SEQ ID NO 14
<211> LENGTH: 36
<212> TYPE: DNA
<213> ORGANISM: Artificial sequence
<220> FEATURE:
<223> OTHER INFORMATION: PCR primer

<400> SEQUENCE: 14
gaattcatgg agtcagacac actgctgcta tgggtg                            36

<210> SEQ ID NO 15
<211> LENGTH: 27
<212> TYPE: DNA
<213> ORGANISM: Artificial sequence
<220> FEATURE:
<223> OTHER INFORMATION: PCR primer

<400> SEQUENCE: 15
ggatccatga tgatgatgat gatggtc                                      27

<210> SEQ ID NO 16
<211> LENGTH: 23
<212> TYPE: DNA
<213> ORGANISM: Artificial sequence
<220> FEATURE:
<223> OTHER INFORMATION: PCR primer

<400> SEQUENCE: 16
ggatccgctc actccagcca cct                                          23

<210> SEQ ID NO 17
<211> LENGTH: 24
<212> TYPE: DNA
<213> ORGANISM: Artificial sequence
<220> FEATURE:
<223> OTHER INFORMATION: PCR primer

<400> SEQUENCE: 17
agatcttcag tctgagtcag gccc                                         24

<210> SEQ ID NO 18
<211> LENGTH: 22
<212> TYPE: DNA
<213> ORGANISM: Artificial sequence
<220> FEATURE:
<223> OTHER INFORMATION: PCR primer
```

```
<400> SEQUENCE: 18
ggatccgagc caggggggag ca                                          22

<210> SEQ ID NO 19
<211> LENGTH: 24
<212> TYPE: DNA
<213> ORGANISM: Artificial sequence
<220> FEATURE:
<223> OTHER INFORMATION: PCR primer

<400> SEQUENCE: 19
agatcttcag tctgagtcag gccc                                        24

<210> SEQ ID NO 20
<211> LENGTH: 26
<212> TYPE: DNA
<213> ORGANISM: Artificial sequence
<220> FEATURE:
<223> OTHER INFORMATION: PCR primer

<400> SEQUENCE: 20
ggatccctga atgaggcctt ggaact                                      26

<210> SEQ ID NO 21
<211> LENGTH: 24
<212> TYPE: DNA
<213> ORGANISM: Artificial sequence
<220> FEATURE:
<223> OTHER INFORMATION: PCR primer

<400> SEQUENCE: 21
agatcttcag tctgagtcag gccc                                        24

<210> SEQ ID NO 22
<211> LENGTH: 24
<212> TYPE: DNA
<213> ORGANISM: Artificial sequence
<220> FEATURE:
<223> OTHER INFORMATION: PCR primer

<400> SEQUENCE: 22
ggatccgagg agccgcagtc agat                                        24

<210> SEQ ID NO 23
<211> LENGTH: 27
<212> TYPE: DNA
<213> ORGANISM: Artificial sequence
<220> FEATURE:
<223> OTHER INFORMATION: PCR primer

<400> SEQUENCE: 23
agatcttcaa atatcgtccg gggacag                                     27

<210> SEQ ID NO 24
<211> LENGTH: 25
<212> TYPE: DNA
<213> ORGANISM: Artificial sequence
<220> FEATURE:
<223> OTHER INFORMATION: PCR primer

<400> SEQUENCE: 24
gaatccgaca ttgtgctgac acagt                                       25
```

```
<210> SEQ ID NO 25
<211> LENGTH: 36
<212> TYPE: DNA
<213> ORGANISM: Artificial sequence
<220> FEATURE:
<223> OTHER INFORMATION: PCR primer

<400> SEQUENCE: 25
ccgcggtcaa tgatgatgat gatgatgatg ggagac                    36

<210> SEQ ID NO 26
<211> LENGTH: 25
<212> TYPE: DNA
<213> ORGANISM: Artificial sequence
<220> FEATURE:
<223> OTHER INFORMATION: PCR primer

<400> SEQUENCE: 26
gaatccgaca ttgtgctgac acagt                                25

<210> SEQ ID NO 27
<211> LENGTH: 24
<212> TYPE: DNA
<213> ORGANISM: Artificial sequence
<220> FEATURE:
<223> OTHER INFORMATION: PCR primer

<400> SEQUENCE: 27
ccgcggtcag tctgagtcag gccc                                 24

<210> SEQ ID NO 28
<211> LENGTH: 25
<212> TYPE: DNA
<213> ORGANISM: Artificial sequence
<220> FEATURE:
<223> OTHER INFORMATION: PCR primer

<400> SEQUENCE: 28
gaatccgaca ttgtgctgac acagt                                25

<210> SEQ ID NO 29
<211> LENGTH: 24
<212> TYPE: DNA
<213> ORGANISM: Artificial sequence
<220> FEATURE:
<223> OTHER INFORMATION: PCR primer

<400> SEQUENCE: 29
ccgcggtcag tctgagtcag gccc                                 24
```